United States Patent
Rouse

(10) Patent No.: US 12,397,244 B1
(45) Date of Patent: Aug. 26, 2025

(54) SYSTEM AND METHOD FOR EXTRACTING NOXIOUS CHEMICALS FROM NATURALLY-OCCURRING RAW MATERIALS AND CREATING USEFUL PRODUCTS

(71) Applicant: Plant Synergies, LLC, Sunriver, OR (US)

(72) Inventor: Michael W. Rouse, Sunriver, OR (US)

(73) Assignee: Plant Synergies, LLC, Sunriver, OR (US)

( * ) Notice: Subject to any disclaimer, the term of this patent is extended or adjusted under 35 U.S.C. 154(b) by 1078 days.

(21) Appl. No.: 17/348,518

(22) Filed: Jun. 15, 2021

Related U.S. Application Data

(60) Provisional application No. 63/040,517, filed on Jun. 17, 2020.

(51) Int. Cl.
*A61L 2/10* (2006.01)
*A01N 65/08* (2009.01)
(Continued)

(52) U.S. Cl.
CPC .......... *B01D 11/0211* (2013.01); *A01N 65/08* (2013.01); *A01N 65/12* (2013.01);
(Continued)

(58) Field of Classification Search
CPC .............................. B02C 23/18; B01J 19/126
See application file for complete search history.

(56) References Cited

U.S. PATENT DOCUMENTS

| 5,238,194 A | 8/1993 | Rouse et al. |
| 5,411,215 A | 5/1995 | Rouse |

(Continued)

FOREIGN PATENT DOCUMENTS

| AU | 2016253568 | 6/2017 |
| CN | 85108918 A | 12/1985 |

(Continued)

OTHER PUBLICATIONS

Accessed first page only) Production of oxalic acid from dry powder of Parthenium hysterophorus L, Ammmj. Agric. Food Chem. 1986, 34, 6, 989-990, Jyoti D. Mane, Sadashiv J. Jadhav and Nanduri A. Ramaiah, Accessed first page only via https://pubs.acs.org/doi/abs/10.1021/jf00072a014 in 2019.

(Continued)

*Primary Examiner* — Bradley R Spies

(74) *Attorney, Agent, or Firm* — McBee, Moore & Vanik IP, LLC

(57) ABSTRACT

A system may be configured to extract useful products from raw materials. Some systems include (1) a wet-grinding apparatus that includes (a) a conveyance for receiving and directing a slurry containing carrier liquids with suspended raw materials, (b) a high torque motor, (c) a motor drive operably coupled to be driven by the high torque motor (d) a set of flat grinding disks that include at least one rotor disk that is operably coupled to be driven by the motor drive, the set configured, when the at least one rotor disk is driven by the motor drive, to accept the slurry from the conveyance, to grind the suspended raw materials, and to discharge the slurry, and (2) a microwave with a microwave emitter configured to emit microwave radiation toward the slurry at least one of before, while, or after the slurry is ground by the wet-grinding apparatus.

34 Claims, 22 Drawing Sheets

(51) Int. Cl.
*A01N 65/12* (2009.01)
*A01N 65/20* (2009.01)
*A61L 2/26* (2006.01)
*B01D 11/02* (2006.01)
*B01D 21/26* (2006.01)
*B01D 21/28* (2006.01)
*B02C 7/02* (2006.01)
*B02C 7/12* (2006.01)
*B02C 21/00* (2006.01)
*B02C 23/10* (2006.01)
*B02C 23/36* (2006.01)
*C10G 1/04* (2006.01)

(52) U.S. Cl.
CPC .............. *A01N 65/20* (2013.01); *A61L 2/10* (2013.01); *A61L 2/26* (2013.01); *B01D 11/0296* (2013.01); *B01D 21/262* (2013.01); *B01D 21/283* (2013.01); *B02C 7/02* (2013.01); *B02C 7/12* (2013.01); *B02C 21/00* (2013.01); *B02C 23/10* (2013.01); *B02C 23/36* (2013.01); *C10G 1/045* (2013.01); *A61L 2202/11* (2013.01)

(56) References Cited

U.S. PATENT DOCUMENTS

| | | | |
|---|---|---|---|
| 5,564,634 A | 10/1996 | Rouse et al. | |
| 6,238,448 B1 | 5/2001 | Rouse et al. | |
| 6,450,935 B1 | 9/2002 | Haworth | |
| 6,634,584 B1 | 10/2003 | Byrne et al. | |
| 6,663,954 B2 | 12/2003 | Rouse | |
| 6,680,110 B1 | 1/2004 | Deeb et al. | |
| 8,168,840 B2 | 5/2012 | Brady et al. | |
| 9,659,748 B2 | 5/2017 | Medoff et al. | |
| 9,677,039 B2 | 6/2017 | Medoff et al. | |
| 9,677,043 B2 | 6/2017 | Medoff et al. | |
| 9,683,249 B2 | 6/2017 | Medoff et al. | |
| 9,683,250 B2 | 6/2017 | Medoff et al. | |
| 9,687,810 B2 | 6/2017 | Medoff | |
| 9,691,510 B2 | 6/2017 | Medoff et al. | |
| 9,700,868 B2 | 7/2017 | Medoff | |
| 9,708,761 B2 | 7/2017 | Medoff et al. | |
| 9,745,518 B2 | 8/2017 | Medoff et al. | |
| 9,745,604 B2 | 8/2017 | Medoff | |
| 9,745,609 B2 | 8/2017 | Medoff | |
| 9,771,520 B2 | 9/2017 | Medoff et al. | |
| 9,777,430 B2 | 10/2017 | Medoff et al. | |
| 9,789,461 B2 | 10/2017 | Medoff et al. | |
| 9,803,222 B2 | 10/2017 | Medoff | |
| 9,816,231 B2 | 11/2017 | Medoff et al. | |
| 9,822,386 B2 | 11/2017 | Medoff | |
| 9,873,897 B2 | 1/2018 | Medoff et al. | |
| 9,920,335 B2 | 3/2018 | Medoff et al. | |
| 9,925,496 B2 | 3/2018 | Medoff et al. | |
| 9,937,478 B2 | 4/2018 | Medoff | |
| 9,957,580 B2 | 5/2018 | Medoff et al. | |
| 9,961,921 B2 | 5/2018 | Medoff | |
| 9,963,727 B2 | 5/2018 | Medoff et al. | |
| 9,963,730 B2 | 5/2018 | Medoff et al. | |
| 9,968,905 B2 | 5/2018 | Medoff | |
| 9,969,938 B2 | 5/2018 | Medoff et al. | |
| 9,970,039 B2 | 5/2018 | Medoff | |
| 10,000,778 B2 | 6/2018 | Medoff | |
| 10,017,801 B2 | 7/2018 | Medoff et al. | |
| 10,035,958 B2 | 7/2018 | Medoff | |
| 10,045,552 B2 | 8/2018 | Medoff | |
| 10,047,384 B2 | 8/2018 | Medoff | |
| 10,047,481 B2 | 8/2018 | Medoff | |
| 10,053,662 B2 | 8/2018 | Medoff et al. | |
| 10,059,035 B2 | 8/2018 | Medoff | |
| 10,066,339 B2 | 9/2018 | Medoff et al. | |
| 10,066,470 B2 | 9/2018 | Medoff | |
| 10,092,890 B2 | 10/2018 | Medoff | |
| 10,105,652 B2 | 10/2018 | Medoff et al. | |
| 10,131,894 B2 | 11/2018 | Medoff et al. | |
| 10,163,535 B2 | 12/2018 | Medoff et al. | |
| 10,173,994 B2 | 1/2019 | Medoff et al. | |
| 10,174,160 B2 | 1/2019 | Medoff et al. | |
| 10,176,900 B2 | 1/2019 | Medoff et al. | |
| 10,202,621 B2 | 2/2019 | Medoff et al. | |
| 11,248,189 B2 | 2/2022 | Stantchev | |
| 2011/0111456 A1* | 5/2011 | Medoff | B01J 19/081 435/68.1 |
| 2011/0178185 A1* | 7/2011 | Blevins | C10G 2/332 518/700 |
| 2014/0011248 A1* | 1/2014 | Medoff | C07D 307/50 549/429 |
| 2016/0264444 A1* | 9/2016 | Zuback | C02F 9/00 |
| 2018/0066293 A1* | 3/2018 | Charron | C08L 97/02 |

FOREIGN PATENT DOCUMENTS

| | | |
|---|---|---|
| CN | 102432420 | 5/2012 |
| CN | 102851119 A | 5/2012 |
| CN | 102675563 | 9/2012 |
| CN | 105111068 | 12/2015 |
| CN | 106977613 A | 1/2016 |
| CN | 107318396 | 11/2017 |
| GB | 705369 | 3/1954 |
| WO | WO2016187581 | 11/2016 |
| WO | WO 2022241073 A1 | 5/2022 |

OTHER PUBLICATIONS (Abstract only) "Chapter 15—Synthesis of Bioethanol From Invasive Weeds: Process Design, Optimization, and Intensification With Ultrasound," Waste Biofinery, Potential and Perspectives pp. 445-485, Shuchi Singh, Arun Goyal, Vijayanand S. Moholkar, Accessed abstract only at https://www.sciencedirect.com/science/article/pii/B978044463992900015X in 2019.

* cited by examiner

SYSTEM AND METHOD FOR EXTRACTING NOXIOUS CHEMICALS FROM NATURALLY-OCCURRING RAW MATERIALS AND CREATING USEFUL PRODUCTS

CROSS-REFERENCE TO RELATED APPLICATION

The present application claims priority to U.S. Provisional Patent Application No. 63/040,517, entitled "System and Method for Extracting Noxious Chemicals from Naturally-Occurring Raw Materials and Creating Useful Products," filed Jun. 17, 2020.

TECHNICAL FIELD

Certain embodiments pertain to a system and method for extracting noxious chemicals from naturally-occurring raw materials. Some particular embodiments pertain to a system and method for extracting noxious chemicals from naturally-occurring raw materials and converting the raw materials into useful products.

BACKGROUND

Many naturally-occurring raw materials have noxious or toxic chemicals that must be extracted before these raw materials can be converted into useful products. Some of these raw materials may be plant stocks of some invasive, toxic, or poisonous plants. These plant stocks often contain noxious or toxic chemicals. For example, many invasive, toxic, or poisonous plants, such as tumbleweed (salsula targus), naturally contain oxalic and di-oxalic acids which are toxic to animals and humans. Other invasive or noxious plants include kudzu, rosemary bean (*Abrus precatorius*) and sage brush. There is a need for systems and methods to extract the noxious or toxic chemicals from plant stocks derived from the above plants and to convert the plant stocks into useful products.

A similar issue arises in the context of petroleum and/or natural gas extraction from sands and similar materials such as shale, zeolite, and sandstone (collectively referred to as "sand"). There is a also a need for systems and methods to extract the petroleum and/or natural gas from the sand.

SUMMARY

The following summary introduces at a high level a limited number of topics described in the Detailed Description. This summary is not intended to identify key or essential features and should not be used for that purpose. In addition, this summary is not intended to be used as a guide to the scope of the claims. Instead, this Summary is provided as an introduction for the reader.

Some embodiments may include a system that is configured to extract useful products from at least one of invasive, a poisonous or a toxic plant stock.

In some embodiments, the system may include at least a wet-grinding apparatus. The wet-grinding apparatus may include at least (1) a fluid conveyance configured for receive and direct a slurry flow that contains at least one or more carrier liquids and at least suspended plant stock, (2) a high torque motor, (3) a motor drive operably coupled to be driven by the high torque motor, (4) a set of flat grinding disks that are operably coupled to be driven by the motor drive and that are configured, when receiving power via the motor drive, to accept the slurry flow, to grind the suspended plant stock, and to discharge the slurry flow, and (5) a fluid outflow configured to receive the discharged ground slurry flow and to evacuate the ground slurry flow to outside the wet-grinding apparatus.

Some embodiments further include at least a microwave unit that includes at least a microwave emitter configured to emit microwave radiation toward the slurry; and wherein the microwave unit is configured to direct microwave radiation toward the slurry at least one of before, while, or after the slurry is ground by the wet-grinding apparatus.

Some additional embodiments provide a method for extracting useful products from at least one of invasive, poisonous or toxic plant stock. In some embodiments the method may include at least conveying a slurry that contains at least one or more carrier liquids and at least some plant stock suspended in the one or more carrier liquids, the conveying being performed at least in part with a conveyance of a wet-grinding apparatus.

In some embodiments the method further includes at least driving at least one disk of a set of flat grinding disks, of the wet-grinding apparatus, with a motor drive coupled with a high torque motor, the driving causing the set of flat grinding disks to accept the slurry on one or more surfaces, to grind the suspended plant stock, and to discharge the slurry;

In some embodiments the method further includes at least receiving the discharged slurry flow and evacuating it outside the wet-grinding apparatus.

In some embodiments the method further includes at least emitting microwave radiation, with at least one microwave emitter, toward at least a portion of the slurry at least one of before, while, or after the suspended plant stock is ground by the wet-grinding apparatus . . .

Some embodiments include a method for extracting useful products from petroleum-based reservoir materials. In some embodiments the method includes at least conveying a slurry that contains at least one or more carrier liquids and at least some petroleum-based reservoir materials suspended in the one or more carrier liquids, the conveying being performed at least in part with a conveyance of a wet-grinding apparatus.

In some embodiments the method further includes at least driving at least one disk of a set of flat grinding disks, of the wet-grinding apparatus, with a motor drive coupled with a high torque motor, the driving causing the set of flat grinding disks to accept the slurry on one or more surfaces, to grind the suspended petroleum-based reservoir materials, and to discharge the slurry.

In some embodiments the method further includes at least receiving the discharged slurry flow and evacuating it outside the wet-grinding apparatus.

In some embodiments the method further includes at least emitting microwave radiation, with at least one microwave emitter, toward at least a portion of the slurry at least one of before, while, or after the suspended petroleum-based reservoir materials is ground by the wet-grinding apparatus.

BRIEF DESCRIPTION OF THE FIGURES

Various embodiments will now be described, by way of example, with reference to the accompanying drawings. It should be noted that these drawings are not necessarily to scale. In addition, the drawings are simplified to avoid obscuring important principles with unnecessary details.

DETAILED DESCRIPTION

Figure 1A:
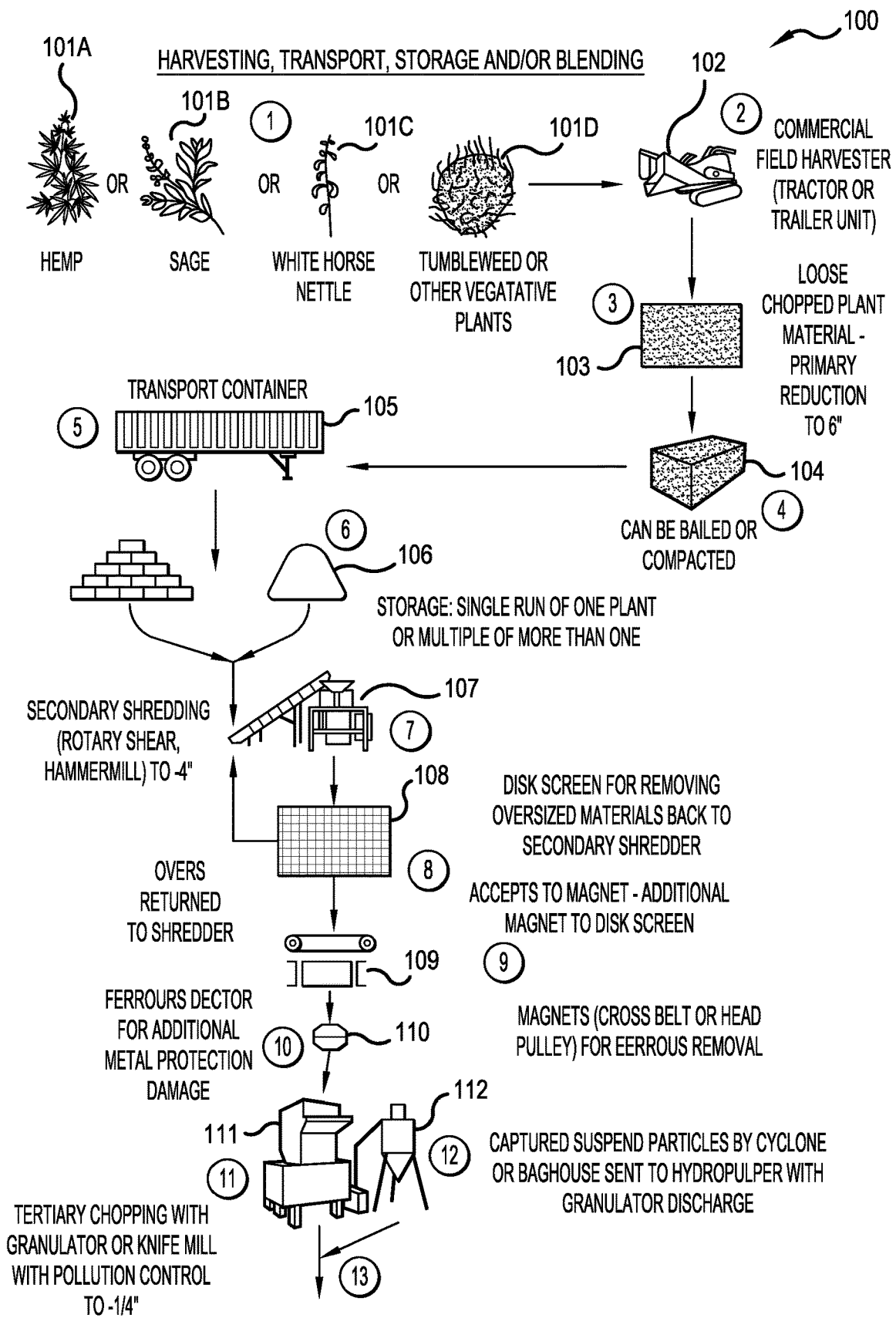
FIGS. 1A thru 1F collectively illustrate a simplified exemplary process for extracting noxious chemicals from naturally-occurring raw materials and converting the raw materials into useful products according to some embodiments. Shown are at least various operations and exemplary equipment for performing the various operations.
Figure 1B:
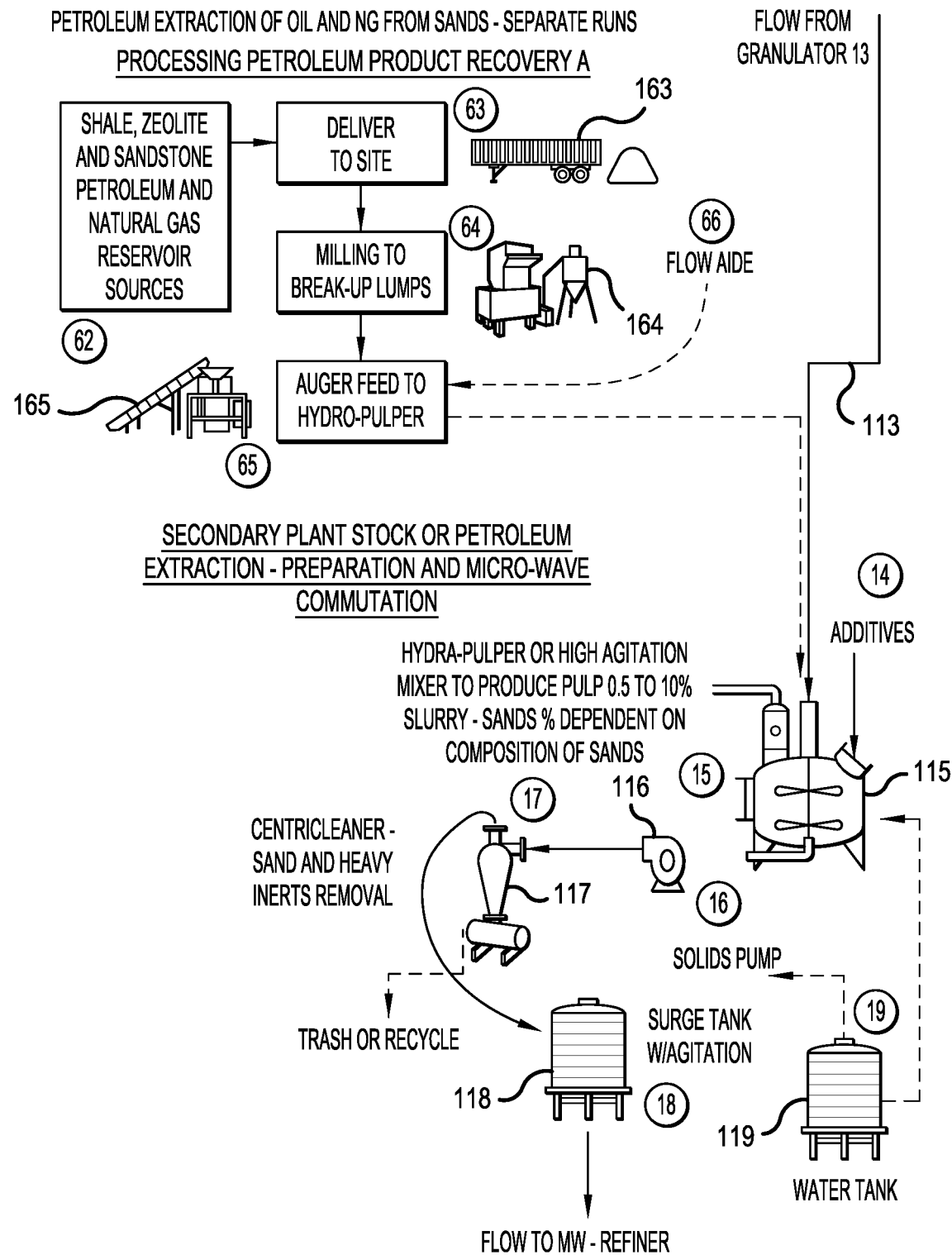

Some embodiments are now described with reference to the above-described figures. In the following description, multiple references are often made to "some embodiments." These references to "some embodiments" are not necessarily referring to the same embodiments, as numerous and varied embodiments are possible. No effort is made to describe all possible embodiments. Sufficient embodiments are described so that those skilled in the art will become appraised of the relevant principles. In addition, disclosed embodiments are not necessarily preferred or advantageous over other embodiments. Accordingly, the scope of the claims is not limited to the disclosed embodiments but instead is limited by the actual language of the claims.

Additionally, in various embodiments those skilled in the art will recognize that various combinations of features are possible. Accordingly, all features described below and referenced in the drawings should be considered optional unless explicitly otherwise indicated. That is, no features should be considered essential unless explicitly indicated.

Invasive plants often have toxic elements that greatly affect their efficacy and in many circumstances may be a threat to our environment from water absorption, poisoning, and vegetation retardation. This application presents a very unique technology that has been developed to convert these plant species into viable commercial products. It is known that the inherent so-called noxious chemicals in these plants can not be fully synthesized. The major chemical component can be compounded into a product but with less effectiveness. All the many other smaller amounts of key chemicals contained in these plants are nearly impossible to be added to a commercial product and when so added the results are a reduced efficacy compared to a naturally produced very green product.

An example of a noxious plant is tumbleweed. When tumbleweed is processed and separated into a liquid byproduct and a wet cellulose byproduct, a variety of useful products are possible. The liquid byproducts of this plant can be very positive in the mite infestation elimination, control and reduction of zebra snails, aphids, and spider mites. The extracted chemicals appear to have minimal to no effect on living organisms such as bees. The cellulose byproduct can be refined into feed pellets, gluten-free flour, and used in direct production of ethanol.

These are just a limited sample of the numerous possible products that can be achieved from just tumbleweed using the principles described herein. A fuller listing of possible products from just tumble weed includes pesticides, insecticides, silage, fungicides, cleaners, solvents, feed pellets, oil forms, vector control products, bleaching agents, thermal fluids, and ethanol and alcohol spirits. Some products could be based on oxalic acid. For example of oxalic acid and is other derivatives can be mixed with sweeteners to attract vectors. Sweeteners could be derived from tumbleweed carbohydrates.

Some embodiments involve initial processing of plant stocks to form a water slurry in which small particles of the plant stocks are suspended. The slurry with the suspended plant stocks is then processed by exposing the plant stocks to a particle reduction by passing the plant stocks suspended in the slurry between flat grinding disks plant stocks to micron and submicron particles in microseconds, thus exposing the whole fiber structure of the plant stocks to release their inherent chemicals instantaneously and at the same time fiber cell structure of the plant stock is greatly expanded by bombarding the particles with microwaves. The water serves as a useful carrier in which additional additives may be added, thus making the final product's a superior compounded product for various product applications. Ultrasonic wave bombardment can also be incorporated into a process to assist with separating the liquid fraction from the wet fiber.

I. Process for Processing Raw Materials-FIGS. 1A-1F

FIGS. 1A thru 1F collectively illustrate a simplified exemplary process 100 for extracting noxious chemicals from naturally-occurring raw materials and converting the raw materials into useful products according to some embodiments. Shown are at least various operations and exemplary equipment for performing the various operations. Those skilled in the art will recognize that many combinations of the operations illustrated in FIGS. 1A thru 1F are possible. Thus, while operations 1 through 71 are shown, depending upon the starting plant stock and the desired final products, in many embodiments not all of these operations are needed. The core operations are as indicated in the independent claims, that is the wet-grinding and one or more of the microwave operations discussed below. Otherwise, the operations described below are optional, non-essential, and may or may not be included in various embodiments. And it is noted also noted that plant stock from some plant species may be processed without microwave treatment consistent with the principles discussed herein.

Indeed, all operations should be regarded as optional. Additionally, although an order or sequence of operations is illustrated, this is not intended to be binding. Again, in many embodiments, depending upon the starting plant stock at the not all of these operations are needed. And they may be performed in sequences other than those shown.

As noted, FIGS. 1A thru 1F also illustrate exemplary equipment that may, in some embodiments, be used to carry out the various operations. The exemplary equipment illustrated are merely examples. Those skilled in the art will recognize that dependent upon a variety of factors, such as conditions in the field, the plant stock being started with, and the desired final product, it may be possible to substitute similar or different equipment for that shown for a particular operation.

Additionally, some of the operations shown in FIGS. 1A thru 1F are applicable to processing plant stock and its derivatives, others are applicable to processing reservoir materials for natural gas and petroleum recovery, and other operations are applicable to both. For ease of discussion and to avoid confusion, this document will first discuss the operations applicable to processing plant stock. Operations applicable only to reservoir material processing will then be discussed.

A. Processing of Plant Stocks

Referencing FIG. 1A, in some embodiments, in Operation 1 invasive, toxic, or poisonous plants such as one or more of hemp 101A, sage 101B, white horse nettle 101C, or tumbleweed 101D, or other vegetative plants may be grown or identified. In some embodiments, a single species like tumbleweed may be harvested.

Operation 2 may include at least harvesting of one or more plant species. In some embodiments the harvesting is performed with a commercial field harvester 102, including a tractor or trailer unit. In some embodiments a single species such as tumbleweed is harvested alone. In other embodiments multiple species may be harvested. Example tumbleweed plus one or more of hemp 101A, sage 101B, white horse nettle 101C.

Operation 3 may include primary reduction. This includes chopping the plant stock to a size of approximately 6 inches to yield reduced plant stock 103.

Operation 4 may include at least bailing or contacting the plant stock to produce bailed or compacted plant stock 104.

Operation 5 may include transporting the plant stock, for example in a transport container 105.

Operation 6 may include storing the plant stock either in a single run of one plant or multiple of more than one type of plant. Stored plant stock 106 may be stored open or closed depending on, for example, product deposition.

Operation 7 may include secondary volume reduction. This may include at least one of shredding, grinding or other volume reduction with secondary reducing equipment 107 (e.g., a rotary shear, a compactor, or a hammer mill, or other reduction equipment). Secondary reducing equipment 107 may also be equipped or associated with ferrous recovery removal devices to prevent damage to writing units and overall contamination.

Operation 8 may include at least using a separator 108 (e.g., disk screen) to remove oversized or stringy branches or lambs back to secondary volume reduction to optimize size reduction efficiency.

Operation 9 may include at least magnet detection with magnetic detector 109 to remove any potential ferrous objects to prevent damage to process equipment downstream.

Operation 10 may include at least using additional magnets 110 (e.g., cross belt magnet or magnetic head pulley) for ferrous removal of small or previously un-removed ferrous objects.

Operation 11 may include at least tertiary reduction of secondarily reduced plant stock by tertiary reducing equipment 111 (e.g. granulator, a grinder, or knife mill) with pollution control. Tertiarily reduced plant stock is of a size and weight suitable for wet-grinding (operation 20) below.

Operation 12 may be performed concurrently with Operation 11 and they include capturing air-suspended particles with air cleaning system 112 (e.g. cyclone or baghouse). Since the tertiary reduction equipment will generally be incorporating an air sweep system using open rotor design, the air carrier passing through the tertiary reduction equipment (e.g., a grinder) should be captured and cleaned with a cyclone or baghouse or a combination of both. The capture particles are then recombined with the outflow tertiary reduction equipment 111.

Operation 13 may include at least transporting tertiarily reduced plant stock via conveyancing equipment 113 (e.g. piping) to mixing apparatus 115.

Operation 14 may include at least adding any additives to tertiarily reduced plant stock. Types of additives are dependent upon the plant stock being processed and the end product desired. Cyclonic centri-cleaner with magnet for removal of unwanted innards and metal from the process downstream may be used.

Operation 15 includes at least mixing plant stock with water to form slurry with a mixing apparatus 115 (e.g., hydra-pulper or high agitation mixer). In some particular embodiments, Operation 15 includes at least mixing dry material with an appropriate water percentage. The appropriate water percentage varies dependent upon a species of plant stock being processed. In some embodiments, sufficient water is added to create a slurry that is between 0.5 and 10 percent by weight. In some embodiments, vapors that are emitted during this stage of the process will be captured and sent to vapor recovery unit (See operation 25 below).

Operation 16 includes at least pumping the slurry with a high pressure head slurry pump 116, ultimately to the wet grind or microwave operations described below.

Operation 17 includes at least removing sand or dirt or similar contaminants from the slurry along with any non-ferrous metals such as copper or aluminum. In some embodiments this is performed with centri-cleaner 117.

Operation 18 includes at least making adjustments for flow or process fluctuations in the slurry flow being pumped via operation 16 above. In some embodiments operation 18 is performed with a surge tank with agitation 118.

Operation 19 includes providing water for the wet grinding operation 21 described below. In some embodiments operation 19 is performed with water tank 119. In some embodiments operation 19 is performed in parallel with operations 17 and 18 described above.

Operation 20 is performed with microwave unit 120 and includes first stage microwave treatment of the slurry with coils inside a microwave chamber. The slurry is treated during a continuous flow of the slurry through the coils. His embodiments, instead of coils, a ceramic constructed tray system may be used inside microwave depending upon the material being processed. This first stage microwave treatment heats and expands plant cells suspended in the slurry for efficient particle commutation in operation 21 below. Some embodiments do not include first stage microwave treatment but instead provide a microwave treatment during or after operation 21. In other embodiments microwave treatment may occur in one or more of operations 20, 21, 22 below. Other embodiments, dependent upon plant species, may not use microwave treatment at all.

Operation 21, a wet-grinding operation, includes at least micro-grinding the plant stock suspended in the slurry while it is still in suspension. It is performed with wet-grinding apparatus 121 (see FIGS. 1C and 2). In some embodiments operation 21 also includes microwave treating the slurry during the wet grinding operation (see discussion of FIG. 2). Wet grinding is performed with either a twin disk or a three disk arrangement, depending on the final product to be produced. A two disk arrangement is one stator stone (a stationary disc) and one rotor disc. A three disk arrangement includes two stator disks on either side of a rotor disc. In some embodiments, the disks are either made entirely of stone or made of a steel alloy with an attached stone grinding surface. In these embodiments, the disks are said to include stone grinding surfaces. The rotor disk is configured to be driven by a motor drive which may include a tube that also carries a flow of slurry for placement of the slurry onto the stone grinding surfaces. Very high shear occurs due to grinding distances between stone grinding services. During operation, the stone grinding faces are only separated by a thin film of the carrier liquid (often water) of the slurry, thus exposing plant cells suspended in the slurry to the shear of the stone grinding faces. This ruptures plant cells while reducing the size of plant stock material in the slurry to less than 100 microns. It also causes release of invasive, toxic, and/or poisonous chemicals from the plant cells into the carrier liquid (e.g., water). Additives added to the slurry may assist this wet grinding process.

Operation 22 is performed with microwave unit 122 and includes a secondary microwave treatment of the slurry similar to operation 20. Microwave unit 122 may be similar to microwave unit 120 except that it is positioned and configured to receive the slurry after operation 21. In some embodiments operation 22 is performed instead of operation 20. In other embodiments operation 22 is performed in addition to operation 20. Either of these operations may be performed in addition or instead of microwave treatment during operation 21. Microwave unit similar to either units 120 or 122 are discussed relative to FIG. 3.

Figure 1C:
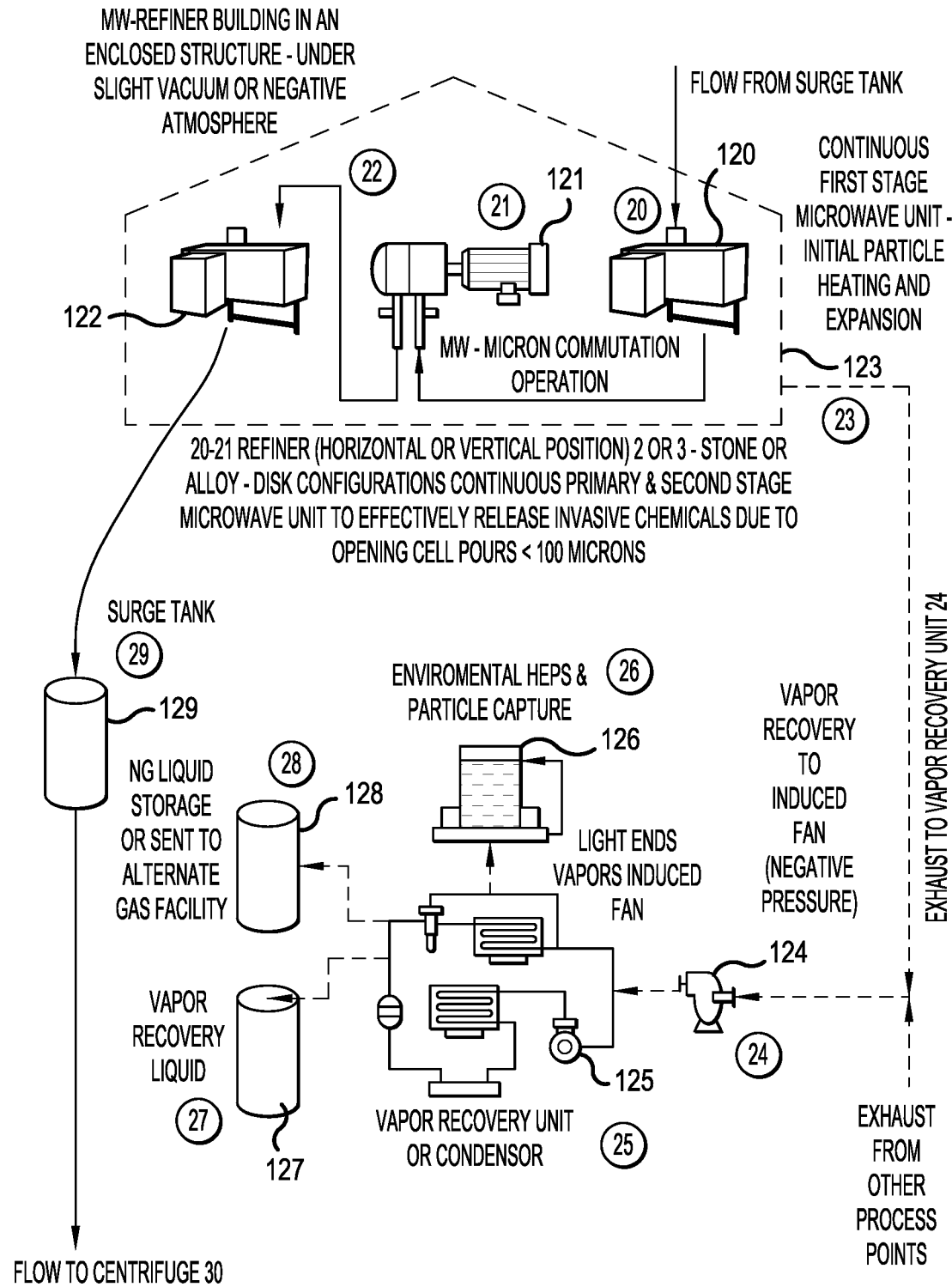
Figure 1D:
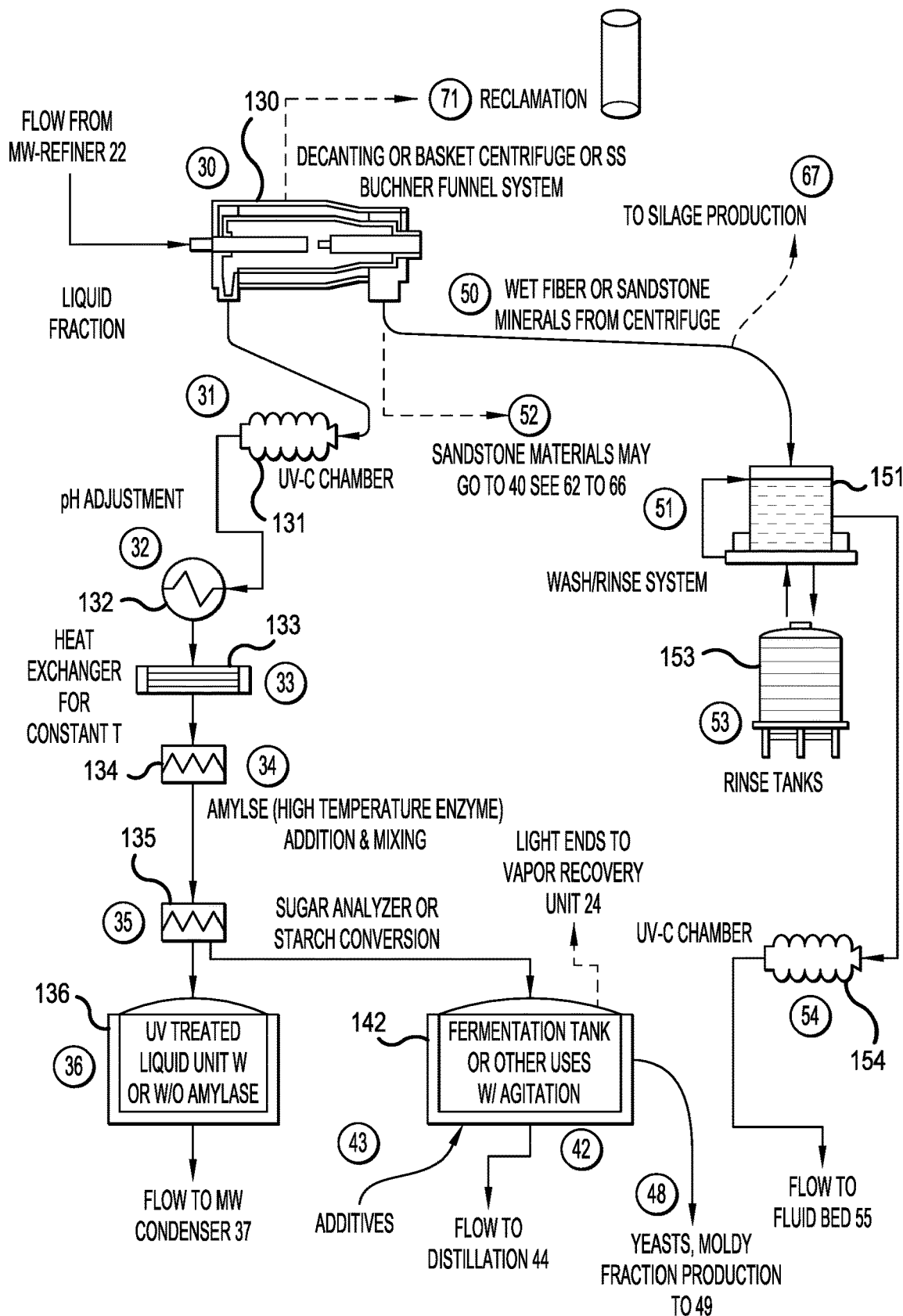

Now described, relative to FIG. 1C, are various operations (23-28) and devices/equipment (123-128) associated with recovery from collective operations 123 (i.e., one or more of operations 120-122).

Operation 23 includes at least collecting vapors off-gassed from one or more of operations 120-122 in one or more containment structures 123 for transporting to vapor recovery unit 125. In some embodiments, one or more of microwave unit 120, wet-grinding apparatus 121, or microwave unit 122 is associated with one or more containment structures 123 configured for capturing off-gassed vapors.

Operation 24 includes creating a negative air pressure in the one or more containment structures and sucking the off-gassed vapors from the one or more containment structures and toward vapor recovery unit 125 (e.g., via one or more of piping, tubing, etc.). Operation 24 is performed with fan 124.

Operation 25 includes at least condensing the off-gassed vapors. This operation is performed with vapor recovery unit 125 (e.g. a condenser).

Operation 26 includes filtering any gases that escape from vapor recovery unit 125 with a HEPA filter 126 or other particle capture.

Operation 27 the recovered liquid from the condensed vapor in storage 127 (e.g a storage container for liquids).

Operation 28 is discussed below relative to petroleum products and processing reservoir materials.

Operation 29 includes at least pumping the slurry (e.g., via pump 116) to a holding tank 129 after the end of collective operation 23.

Operation 30 includes at least receiving process slurry from holding tank 129 and separating at into a liquid fraction and a wet fiber. This operation is performed with separator apparatus 130 (e.g. one or more of a decanter, a basket centrifuge, or an SS Buchner funnel system). Ultrasonics may be employed with an SS Buchner funnel system to facilitate separation into the liquid fraction and the wet fiber. The liquid fraction may include chemicals such as oxalic acid and/or other plant derived chemicals.

The remainder of the operations to be described include either processing of the liquid fraction or processing of the wet fiber. Processing of the liquid fraction starts with operation 31 and processing of the wet fiber begins with operation 50. The description below first describes the operations associated with processing the wet fraction, beginning with operation 31. The description then returns to operation 50 and the describes processing of the wet fiber.

1. Liquid Fraction Processing

Operation 31 includes at least subjecting the decanted liquid fraction with ultraviolet light (at least in ultraviolet chamber 131 with an ultraviolet emitter) on a continuous basis to kill germs or prevent growth of bacteria. In some embodiments the author of life is UV-C. In some embodiments the wavelength of the ultraviolet light is between 100 and 3000 nanometers.

Operation 32 includes at least adjusting, via pH adjustment equipment 132 (e.g. an additive mixer) of the liquid fraction by adding or mixing acidic or caustic additives.

Operation 33 includes at least with a heat exchanger 133 for optimal amylase exchange and effectiveness. Amylase being a high temperature enzyme that requires a optimal temperature range for effectiveness. This operation and operation 34 below are not performed if amylase is not added-again dependent upon desired end products and beginning raw materials.

Operation 34 includes at least adding amylase to the now heated liquid fraction with inline mixer 134. This operation includes metering and dispersing amylase type products.

Operation 35 includes at least analyzing sugars in liquid fraction for viscosity and/or specific gravity. This operation is performed with analyzing equipment 135. Dependent upon the desired end product, the liquid fraction may be diverted to operation 42 (fermentation) described below.

Operation 36 includes at least storing, in storage 136, ultraviolet-treated liquid fraction-which may nor may not include amylase.

Operation 37 includes at least concentrating the liquid fraction into concentrated densities and concentrated fractions with liquid concentrator 137, which includes treatment with microwave radiation and ultrasonic waves. Liquids with concentrated densities and concentrated fractions may include concentrated liquids and high viscosity liquids in the form of a syrup or an oil emulsion. The concentration of the liquid improves economic value and greater efficiency in further processing, for example in operation 41 below for processing into final products such as liquids, syrups, and/or oils. Vapors off gassed from this operation are transported to vapor recovery unit 25.

Operation 38 includes online mixing with online mixer 138 of additives into the liquid fraction.

Operation 39 includes at least crystallizing the remaining liquid fraction at least in part with microwave crystallizer and granulator 139 to convert the remaining liquid fraction to crystals.

Operation 40 includes packaging and/or final processing of crystals of operation 39 into final products within crystals facility 140. These final products may be a combination of the extracted oxalic derivatives in a sugar form for direct use (e.g., as pesticides, or other pest control) or for resolubilization for spray applications. This is the final operation for these products.

Operation 41 receives concentrated liquids and high viscosity liquids at facility 141 from operation 37 for final packaging as liquid, theory of spirit, and oils. This is the final operation for these products.

Operation 42 includes at least receiving liquid with starches and sugars analyzing operation 35 and fermenting these liquids in fermentation tank 142. In some embodiments fermentation tank 142 provides agitation as well as fermentation. This operation includes converting the liquid fraction (or a portion thereof) into alcohol via starch reduction of plant stock starches to a sugar. Vapors off gassed from operation 42 are transported to vapor recovery unit 25.

Operation 43 includes at least adding additives to fermentation tank 142 while liquid is fermenting in operation 42.

Operation 44 includes at least decanting and distilling the fermented liquid from operation 42 with distiller 144. Off-gassed vapors are transported to vapor recovery unit 125. This operation produces a distilled liquid which moves to operation 46. This operation also produces bottoms which are a dry fraction.

Operation 45 includes at least sending the dry fraction from operation 44 to solids stream as a solid waste product.

Operation 46 includes at least receiving ethanol from operation 45. For some of the ethanol is for an ethanol product and this is a final operation. For some other ethanol moves to operation 47.

Operation 47 includes at least producing specialized spirits such as whiskies, brandys, gin and vodka from some of the ethanol from operation 46. This is a final operation for these products.

Operation 48 includes at least separating yeasts and moldy fraction from fermentation tank 142 and moving towards operation 49. These items may also be reused in operation 42 in further fermentation.

Operation 49 includes at least receiving the yeasts and moldy fraction 149 as final products. This is a final operation for these products.

2. Wet Fiber Processing

Discussion now returns to the processing of the wet fiber produced in operation 30. The discussion begins with operation 50.

Operation 50 includes at least obtaining wet fiber as an output of operation 30 and transporting to operation 51. Alternatively or additionally, Operation 50 includes at least transporting the wet fiber to operation 67 (transporting to silage production), discussed below.

Operation 51 includes at least washing the wet fiber in a wash system 151. Water may be reused from one or more wash tanks of the wash system 151.

Operation 52 is discussed later regarding petroleum products.

Operation 53 includes at least rinsing the web fiber in rinse system 153 (including at least rinse tanks, as depicted).

Operation 54 includes at least treating washed and rinsed fiber with UV-C radiation (e.g., with ultraviolet (UV-C) chamber 154 configured with ultraviolet emitter) to prevent bacterial growth from the wash and rinse.

Operation 55 includes at least drying the wet fiber with a drying system 155 (including at least one or more of fluid bed, tray drier, rotary drier, or flash dryers for removal of moisture. Off-gassed vapors from drying operation may be sent to vapor recovery unit 25. Operations 56 and 57 are discussed below relative to petroleum products.

Operation 58 includes at least adding additives to the dry fiber. Some additives may be from previously processed plant stock.

Operation 59 includes at least mixing additives into dry fiber with mixer 159 (may also include compounding). These additives assist with dispersion of final products.

Operation 60 includes at least receiving output from operation 59 as gluten free powder. This is a final operation for this final product.

Operation 61 includes at least receiving output of operation 59 and pelletizing it (e.g., with pelletizing and processing unit 161) as one or more of feed pellets or processing into one or more industrial powders. This product may incorporate silage from operation 68 discussed below regarding petroleum products. Incorporating the silage into these products is operation 70.

Operations 62-66 are discussed below relative to petroleum products.

As discussed above, operation 67 includes at least transporting at least some of the wet fiber separated in operation 30 for silage production in operation 68. For at least some of the wet fiber, Operation 67 is an alternative to operation 50, as discussed above.

Operation 68 includes at least fermenting the wet fiber in an anerobic atmosphere in enclosed silage mixer 168 for conversion of starches to sugar. This conversion of starches to sugars significantly improves the taste and appeal of this as animal feed and reduction of storage time. Additional solid waste from this process may be added to the silage since obnoxious elements are removed at various operations.

Operation 69 includes at least slowly releasing one or more inert gases (e.g., from gas cannister 169) to the bottom of enclosed silage mixer 168 via porous piping or tubing.

This introduction of the one or more inert gases into the moist silage improves silage conversion in an anaerobic atmosphere.

Operation 70 includes at least transporting finished silage to pelletizing and processing unit 161 for incorporation into pellets and/or powders. This is a final operation for these products and the final operation for this process 100.

B. Processing of Petroleum/Natural Gas Reservoir Materials for Petroleum Products Preliminarily it is noted that reservoir materials composed largely of sedimentary rocks can be processed using many of the same operations as for the plant stock. Often natural gas and oil are found in sedimentary rocks that were formed when grains and mineral particles were deposited by running water and fused together. Because these rocks are cemented together from such small components, they are porous, full of spaces in which energy-rich carbon compounds can settle, later to be liberated in the form of either oil or gas. Processing of reservoir materials begins with operation 62 below. The processing after operation 62 replaces operations 1-13 discussed above relative to processing of plant stock.

Operation 62 includes at least extracting reservoir materials such as shale, zeolite, and/or sandstone from petroleum and natural gas reservoir sources.

Operation 63 includes at least delivering the reservoir materials 164 to a processing site at least in part with transporting equipment 163 (e.g., via conventional oil field transport vehicles or containers).

Operation 64 includes at least milling the reservoir materials 164 with milling equipment 164 (e.g. a hammermill type machine followed by a rod ball mill to fluff the materials). Most reservoir materials are very friable and have a consistency of sand and may be oily to touch. These materials are easily milled as discussed above.

Operation 65 includes at least transporting milled materials via transport equipment 165 (e.g., a auger feeder) to operation 15.

Operation 66 includes at least adding a flow aide additive to the milled materials in tandem with operation 65. One flow aid would be trace amounts of silica.

Operation 15 is discussed above relative to processing of plant stocks and applies similarly here regarding petroleum materials. Amount of added water (or other carrier liquid) varies dependent on composition of sands. And therefore the percent of sand by weight of the slurry will also vary.

After operation 15, processing of the reservoir materials proceeds to operations 16, and 18-30 with modifications as discussed below. Unless otherwise indicated these operations are unchanged from as discussed above relative to plant stocks. However, in some embodiments operation 17 is not used for processing reservoir materials.

At one or more of operations 20-22, slurry is processed as discussed above.

Combination of microwave treatment and wet-grinding reduces suspended particles in the slurry to 100 microns or less and causes release of petroleum chemicals in the suspended materials. These operations yield an off-gassed vapor including at least natural gas. This vapor is transported for processing according to operations 24-27 as discussed above. Additionally, at operation 28, natural gas that is condensed from the vapor is stored (e.g., in tanks 128) from where it can be transported to a natural gas facility.

After processing in one or more of operations 20-22 the processed slurry moves to operation 29 as discussed above and then to operation 30.

Operation 30 proceeds as discussed above. With respect to the processed reservoir materials, operation 30 yields a liquid fraction that includes at least petroleum, a dry fraction that includes at least sand and other reservoir materials. For the wet fraction, processing moves to operation 71 reclamation, for example with reclamation tank 171. For the dry fraction, processing moves via a transport operation 52 to operation 40 where crystals and other materials are a final product and processing ends. Alternatively, processing for the dry fraction moves to operations 56 (transport) and 57 (drying of sandstone, zeolite, and similar materials with drying system 155) an end operation. Optionally, processing for the sandstone, zeolite, and similar materials may include operations 51 and 53 (wash and rinse), discussed above, and then to operation 57.

II. Exemplary Wet-Grinding Apparatus with Microwave Unit-FIG. 2

An exemplary wet-grinding apparatus 201 is now discussed with reference to FIG. 2. As is explained below, this wet-grinding apparatus includes one rotary disk 210 and one stator disk 209. This embodiment may be compared with the wet-grinding apparatus of FIG. 4 which includes two stator disks.

Figure 2:
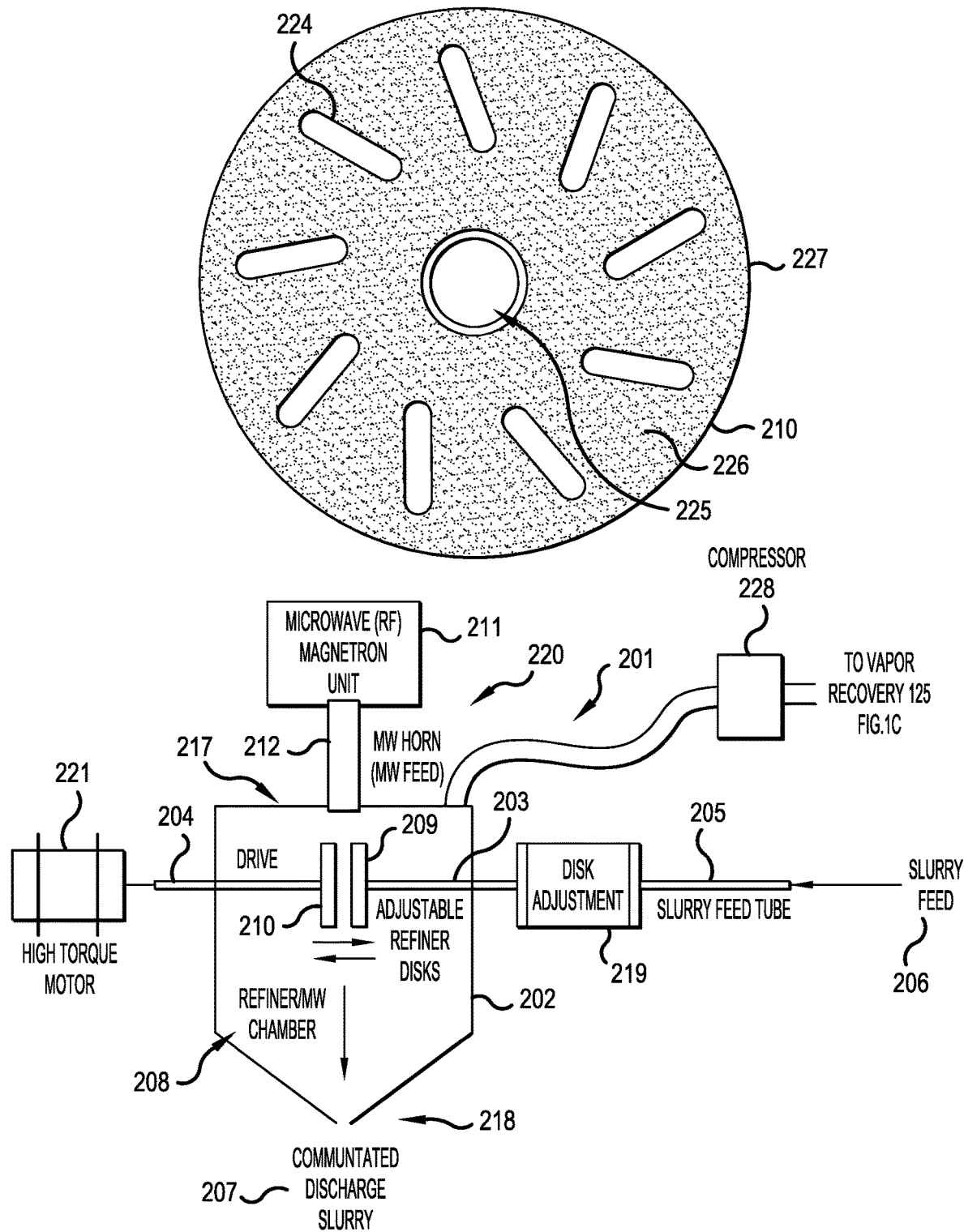
FIG. 2 is a simplified schematic diagram, consistent with some embodiments, of a wet-grinding apparatus with a rotary and a stator disc, an attached microwave magnetron unit and an encasement for wet-grinding and microwaving slurry. Shown in simplified form are at least components of the wet-grinding apparatus, including an exemplary disk with grooves.

Referencing FIG. 2, a wet-grinding apparatus 201 includes at least a fluid conveyance 205 (e.g., slurry feed tube as shown) configured for receive and direct a slurry flow 206 (e.g., slurry feed) that contains at least one or more carrier liquids and at least suspended plant stock.

The exemplary wet-grinding apparatus 201 further includes at least a high torque motor 221 (refiner motor as shown) and a motor drive 204 operably coupled to be driven by the high torque motor 221.

The exemplary wet-grinding apparatus 201 further includes at least a set 217 of flat grinding disks (e.g., stator disk 209 and rotor disk 210) that include at least one rotary disk 210 that is operably coupled to be driven by the motor drive 204 and that are configured, when the at least one rotor disk is receiving power via the motor drive, to accept the slurry flow 206, to grind the suspended plant stock (e.g., plant parts 703 of FIG. 7), and to discharge the slurry flow 206. In the exemplary wet-grinding apparatus 201 conveyance 205 is coupled with disk adjustment 219 and with stator disk 209. Disk adjustment 219 adjusts a length of a portion 203 of conveyance 205 that determines how close stator disk 209 is to rotor disk 210. When in operation only a thin layer of slurry should separate disks 209 and 210. Slurry may then escape from conveyance 205 between disks 209 and 210 for grinding of the suspended plant stock between disks 209 and 210.

The exemplary wet-grinding apparatus 201 further includes at least a fluid outflow 218 configured to receive the discharged ground slurry flow 207 and to evacuate the ground slurry 207 (e.g., a commutated discharge slurry) flow to outside the wet-grinding apparatus 201.

The exemplary wet-grinding apparatus 201 further includes at least a microwave unit 220 that includes at least a microwave emitter 211 (e.g., a microwave (RF) magnetron unit) configured to emit microwave radiation toward the slurry (e.g., with microwave horn 212 (MW feed). Microwave radiation and off-gassed vapor are contained within chamber 208 by containment structure 202. Off-gassed vapors are captured via negative atmospheric pressure within containment structure 202 by compressor 228 and directed toward vapor recovery unit 125 (e.g., at least a condenser).

FIG. 2 further illustrates an enlarged side view of rotor disk 210. However, the structures shown would be at least similar for stator disk 209. Rotor disk 210 includes an axial hole 225, a grinding surface 226, an outer perimeter 227, and grooves or slots 224 for assisting flow of slurry over the grinding surfaces 226. In some embodiments grooves or slots are not present as they are not needed for processing of some raw materials.

III. Exemplary Standalone Microwave Unit-FIG. 3

Figure 3:
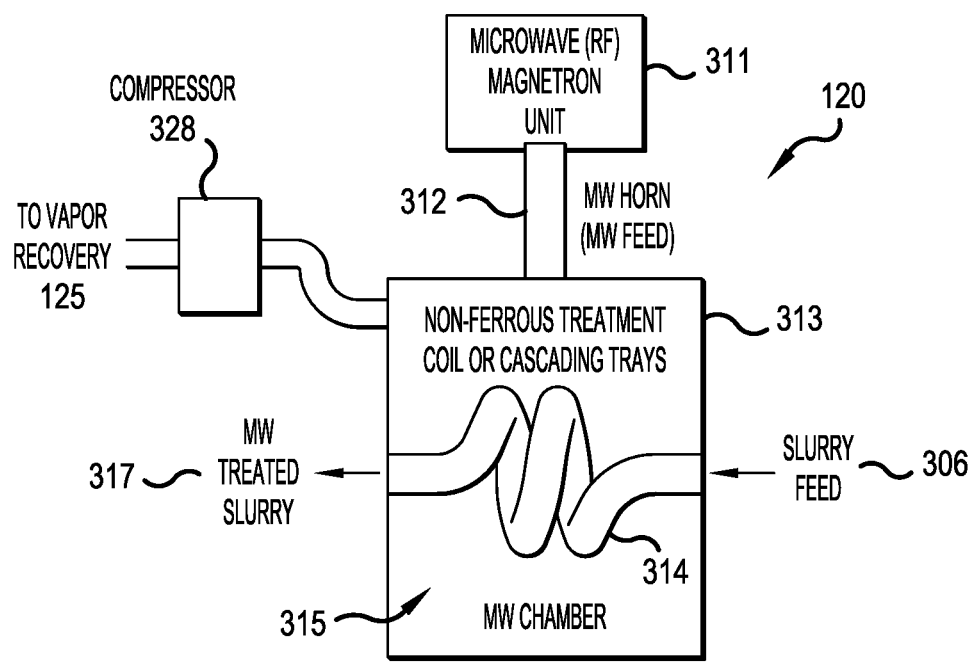
FIG. 3 is a schematic diagram, consistent with some embodiments, of a standalone microwave for treating slurry with microwave radiation. Shown are at least a microwave magnetron unit, a microwave chamber, and a non-ferrous treatment coil.

Referencing FIG. 3, an exemplary standalone microwave unit 120 is shown.

Standalone microwave unit 120 is configured to provide microwave treatment in operation 20 of process 100 discussed above. But standalone microwave unit 120 could also function as microwave unit 122 to perform operation 22.

Figure 4:
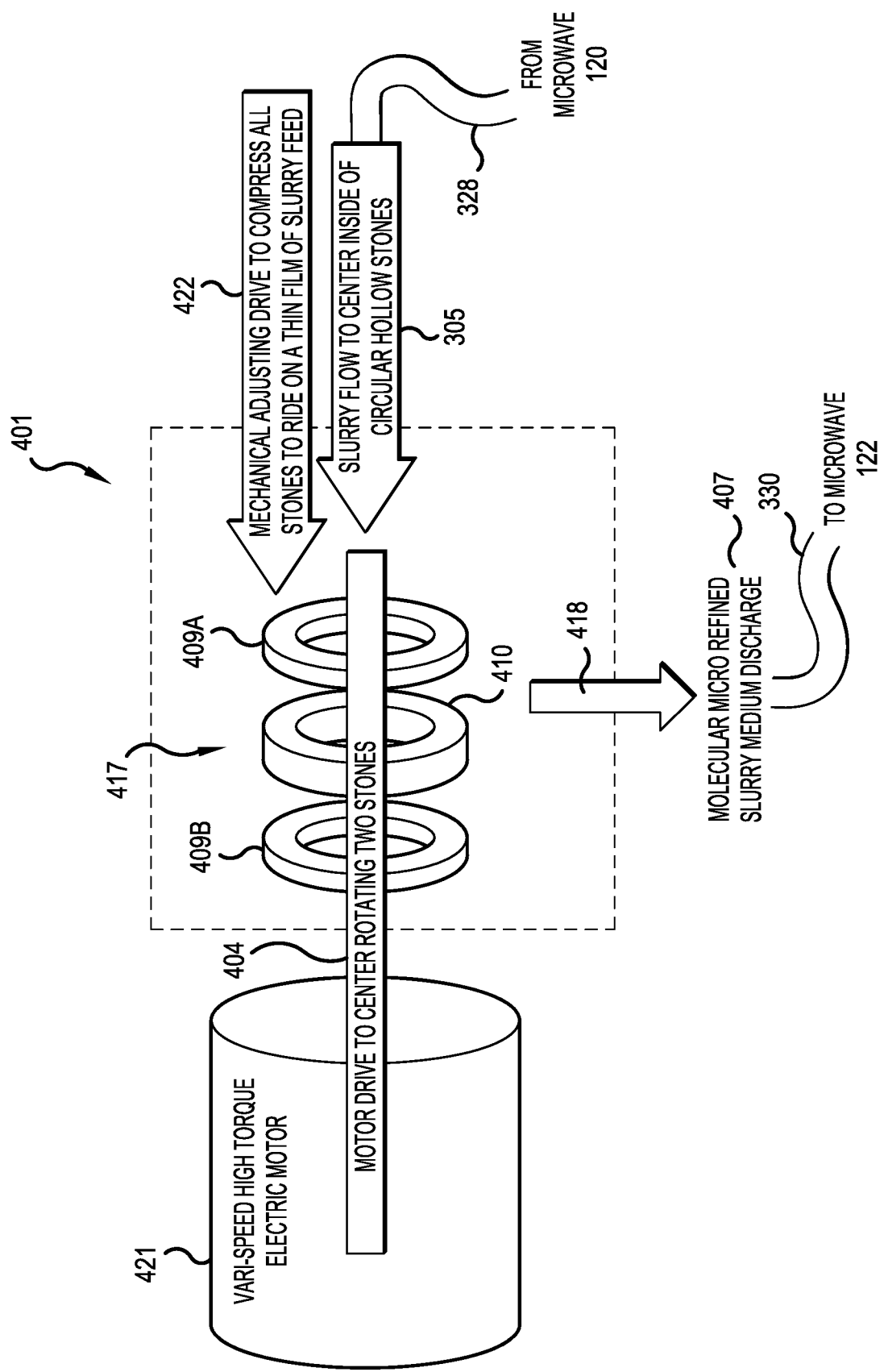
FIG. 4 is a schematic diagram, consistent with some embodiments, of a wet-grinding apparatus with one rotary disk and two stator disks for wet-grinding a slurry.

In some embodiments, an exemplary microwave unit is separate from a wet-grinding apparatus (e.g., 201 or 401 of FIG. 4).

The exemplary microwave unit 120 includes at least one or more high temperature-resistant conveyances 314 (e.g., tubes or pipes as shown, but could also be trays) that include at least one of tubes, coils, or troughs that are transparent to microwave radiation and that are further configured for receiving and conveying the slurry flow (e.g., slurry feed 306 and microwave-treated slurry 317).

The exemplary microwave unit 120 includes at least a microwave emitter 311 positioned to emit microwave radiation toward (e.g. via microwave horn 312) at least a portion of the one or more conveyances 314. The emitter 311 being coupled with microwave horn 312 for aiming the microwave radiation. The one or more conveyances 314 being at least partially disposed with a microwave containment structure 313 defining a chamber 315 for containing the microwave radiation and vapors off-gassed from slurry. Compressor 228 is configured for creating a negative atmosphere within chamber 313 and for siphoning off-gassed vapors toward vapor recovery 125 (e.g., of FIG. 1C).

It being noted that when the microwave emitter is in operation the emitted microwave radiation cause cells 723 of the ground plant stocks within the one or more conveyances to expand thereby making a wet-grinding more effective (See discussion regarding FIG. 7 below).

IV. Exemplary Wet-Grinding Apparatus-FIG. 4

An exemplary wet-grinding apparatus 401 is now discussed with reference to FIG. 4. As is explained below, this wet-grinding apparatus includes one rotary disk 410 and two stator disks 409A and 409B. This embodiment may be compared with the wet-grinding apparatus of FIG. 2 which includes one stator disks. This embodiment also differs from the wet-grinding apparatus 201 of FIG. 2 because it does not include a built-in microwave unit 220. Instead, it includes a feed 328 from a microwave unit 120 and a feed 330 to microwave unit 122.

Referencing FIG. 4, a wet-grinding apparatus 401 includes at least a fluid conveyance 305 (e.g., slurry flow bringing microwave unit 120 of FIG. 3) configured for receive and direct a slurry flow that contains at least one or more carrier liquids and at least suspended plant stock (in some embodiments between 1% and 25% suspended plant stock by weight).

The exemplary wet-grinding apparatus 401 further includes at least a high torque motor 421 (e.g., a vari-speed high torque electric motor) and a motor drive 404 operably coupled to be driven by the high torque motor 421.

The exemplary wet-grinding apparatus 401 further includes at least a set 417 of flat grinding disks (e.g., stator disks 409A and 409B and rotor disk 410) that include at least one rotary disk 410 that is operably coupled to be driven by the motor drive 404 and that are configured, when the at least one rotor disk is receiving power via the motor drive 421, to accept the slurry flow, to grind the suspended plant stock (e.g., plant parts 703 of FIG. 7), and to discharge the slurry flow. In the exemplary wet-grinding apparatus 401 mechanical adjusting drive 422 is configured to compress all disks (e.g., stator disks 409A and 409B and rotor disk 410) to ride on thin films of slurry. When in operation only thin layers of slurry should separate stator disks 409A and 409B and rotor disk 410. Slurry may then escape from conveyance 305 between stator disks 409A and 409B and rotor disk 410 for grinding of the suspended plant stock between 409A and 409B and rotor disk 410.

As discussed above, in some embodiments one or more of stator disks 409A and 409B and rotor disk 410 are composed of a steel alloy. In other embodiments one or more of stator disks 409A and 409B and rotor disk 410 are composed of stone or stone-like materials such as silicon carbide, aluminum oxide, zirconia, or ceramic friable mixes. In some embodiments one or more of stator disks 409A and 409B and rotor disk 410 are composed partly of a steel alloy, but with an attached stone facing to provide the grinding surfaces.

The exemplary wet-grinding apparatus 401 further includes at least a fluid outflow 418 configured to receive the discharged ground slurry flow and to evacuate the ground slurry 407 flow to outside the wet-grinding apparatus 401.

The exemplary wet-grinding apparatus 401 is flowingly coupled (e.g. via feed 328) to receive microwave-treated slurry from microwave unit 120. This exemplary wet-grinding apparatus 401 is additionally flowingly coupled (e.g. via feed 330) to provide ground slurry 407 to microwave unit 122.

V. Process for Processing Invasive, Poisonous or Toxic Plant Stock-FIG. 5

Figure 5:
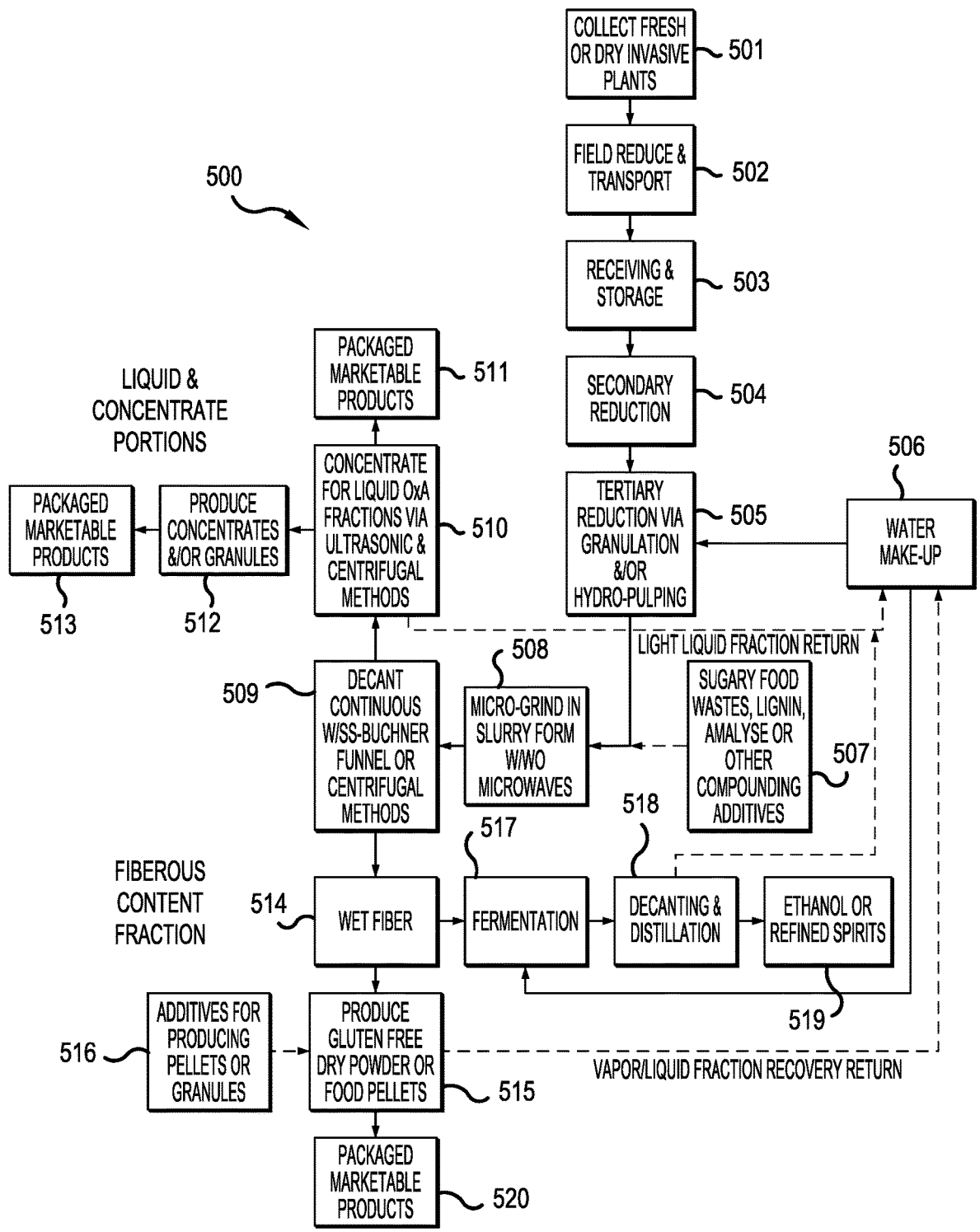
FIG. 5 is a flow diagram showing an exemplary process for extracting noxious chemicals from at least one of invasive, a poisonous or toxic plant stock and converting the plant stock and the extracted noxious chemicals into useful products according to some embodiments.

An exemplary process 500 for processing invasive, poisonous, and/or toxic plants into useful products is now described relative to FIG. 5.

Referencing FIG. 5, operation 501 includes at least collecting at least one of fresh or dry plants. The collected plants could include many invasive, poisonous, and/or toxic plants, such as, for example, hemp, sage, white horse nettle, tumbleweed. The collected plants could also include combinations of one or of the above or of other plants.

Operation 502 includes at least field reduction and transport of the collected plants. The field reduction could include primary reduction. In some embodiments primary reduction includes at least chopping the plants to one or more sizes in of approximately 6 inches. Transport could include transport via a transport container (e.g., 105 of FIG. 1A)

Operation 503 includes at least receiving and storing the primary reduced plants from operation 502. Stored plant stock may be stored open or closed depending on, for example, product deposition.

Operation 504 includes at least secondary reduction. This may include at least one of shredding, grinding or other volume reduction with reducing equipment (e.g., 107 of FIG. 1A, which could be a rotary shear or a hammer mill, or other reducing equipment know to those skilled in the art).

Operation 504 may also include removal of ferrous objects (e.g., ferrous metal debris) with removal equipment (e.g., magnets).

Operation 505 includes at least tertiary reduction with tertiary reduction equipment (e.g., 111 of FIG. 1A), such as a granulator a knife mill. Additionally a hydro-pulper or high agitation mixer is used to add a carrier liquid (e.g., water from operation 506 below) to create a slurry that includes at least tertiarily-reduced and suspended plant stock and the carrier liquid. In some embodiments, this carrier liquid is between 1% and 25% suspended plant stock by weight.

Operation 506 includes at least providing water to a hydro-pulper of operation 505 (discussed above) and/or to fermentation operation 517 (discussed below). Water for operation 506 may be received from one or more of operations 510, 515, 516, or 518 described below. Operation 506 may also include using a vapor recovery system to condense water vapor (produced in one or more of operations 510, 515, 516, or 518) into water.

Operation 507 includes at least adding at least one of sugary food wastes, lignin, amalyse or other compounding additives to the slurry. This operation is dependent upon the plant stock being processed and the end products desired and may not be used in some embodiments.

Operation 508 includes at least wet-grinding (e.g., may also be called micro-grinding) the slurry with or without microwave treatment. This operation is at least similar to operation 21 discussed above.

Operation 509 includes at least separating the wet-ground slurry from operation 508 into a liquid fraction and wet fiber. This operation may be performed with separator apparatus 130 of FIG. 1D (e.g., with one or more of a decanter, a basket centrifuge, or an SS Buchner funnel system). The liquid fraction may include chemicals such as oxalic acid or similar acids. The wet fiber may include fibrous plant stock residue. Processing of the liquid fraction moves forward with operation 510 (below) and processing of the wet fiber moves forward with operation 514 below.

Operation 510 includes at least concentrating the liquids, such as liquid oxalic acid, via one or more of ultrasonic wave treatment, microwave radiation, and centrifugal methods. Vapors off-gassed from this operation are transported (e.g., via piping and/or tubing) to a vapor recovery operation associated with operation 506.

Operation 511 includes at least packaging of finished products from operation 510 such as oxalic acid.

Operation 512 includes at least producing at least one of concentrates or granules. These products are packaged in operation 513.

Returning to processing of the wet fiber (process block 514), operation 515 includes producing at least one of gluten-free dry powders or food pellets from at least a portion of the wet fiber produced in operation 509. This operation includes at least drying the wet fiber.

Operation 516 includes at least providing additives for producing pellets or granules from operation 515.

Operation 520 includes at least packaging the at least one of gluten-free dry powders or food pellets from operation 515 into final products.

Operation 517 includes at least fermenting at least a portion of the wet fiber produced in operation 509. Water is added via operation 506. A fermented beverage is produced.

Operation 518 includes at least decanting and distilling the fermented beverage of operation 517.

Operation 519 includes packaging and final preparation of at least one of ethanol and refined spirits.

VI. Extractor-FIG. 6

Figure 1E:
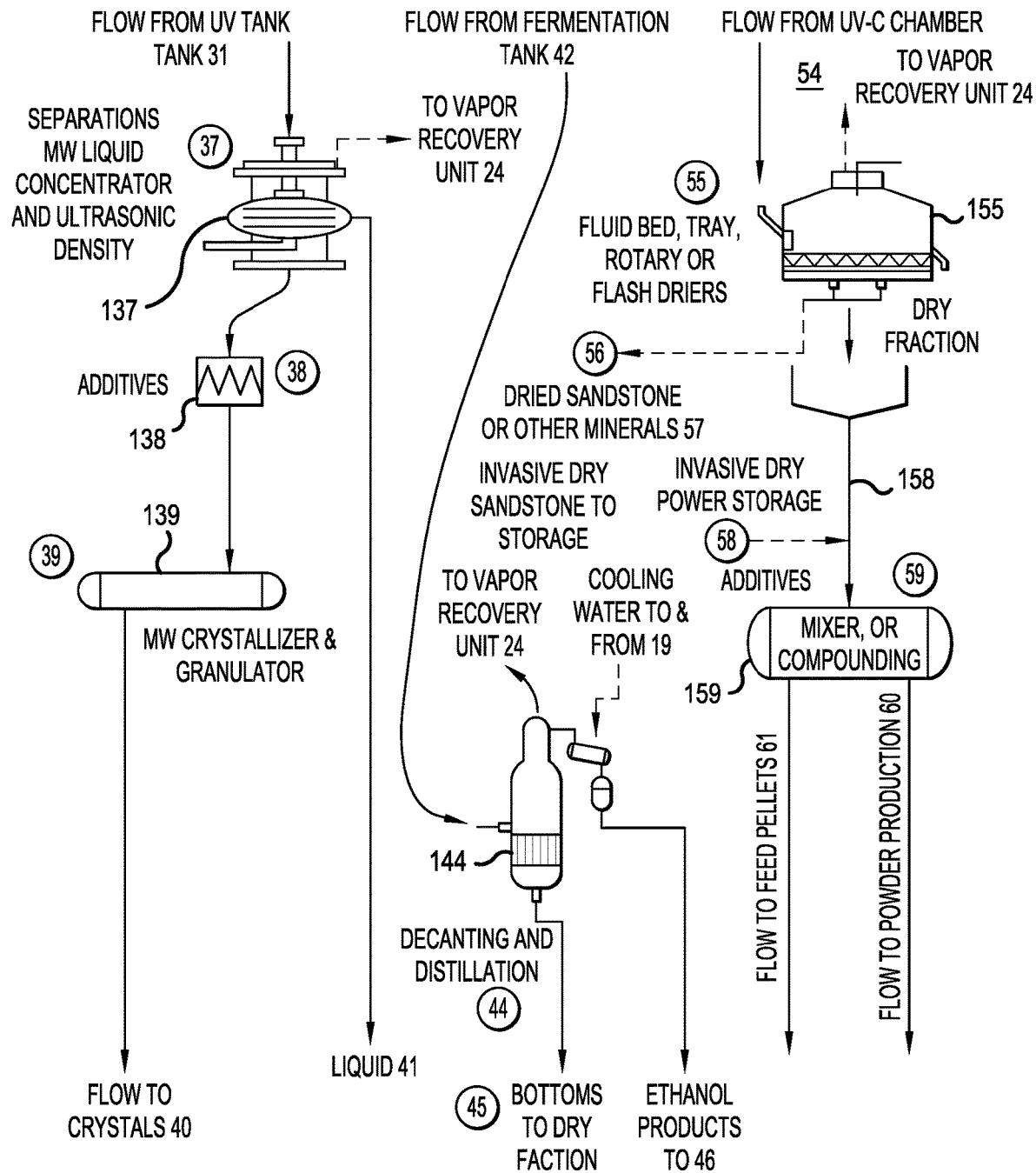
Figure 1F:
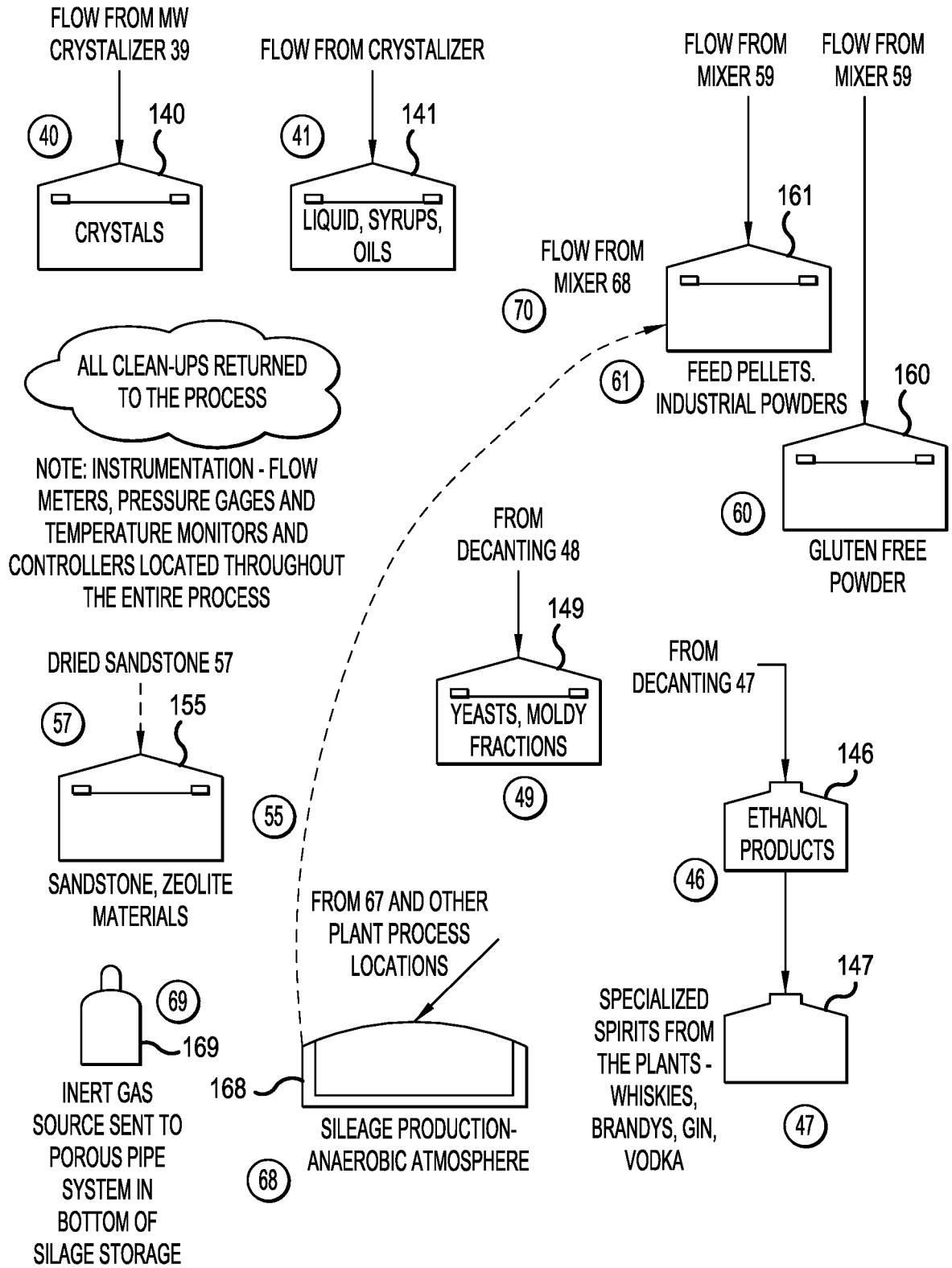
Figure 6:
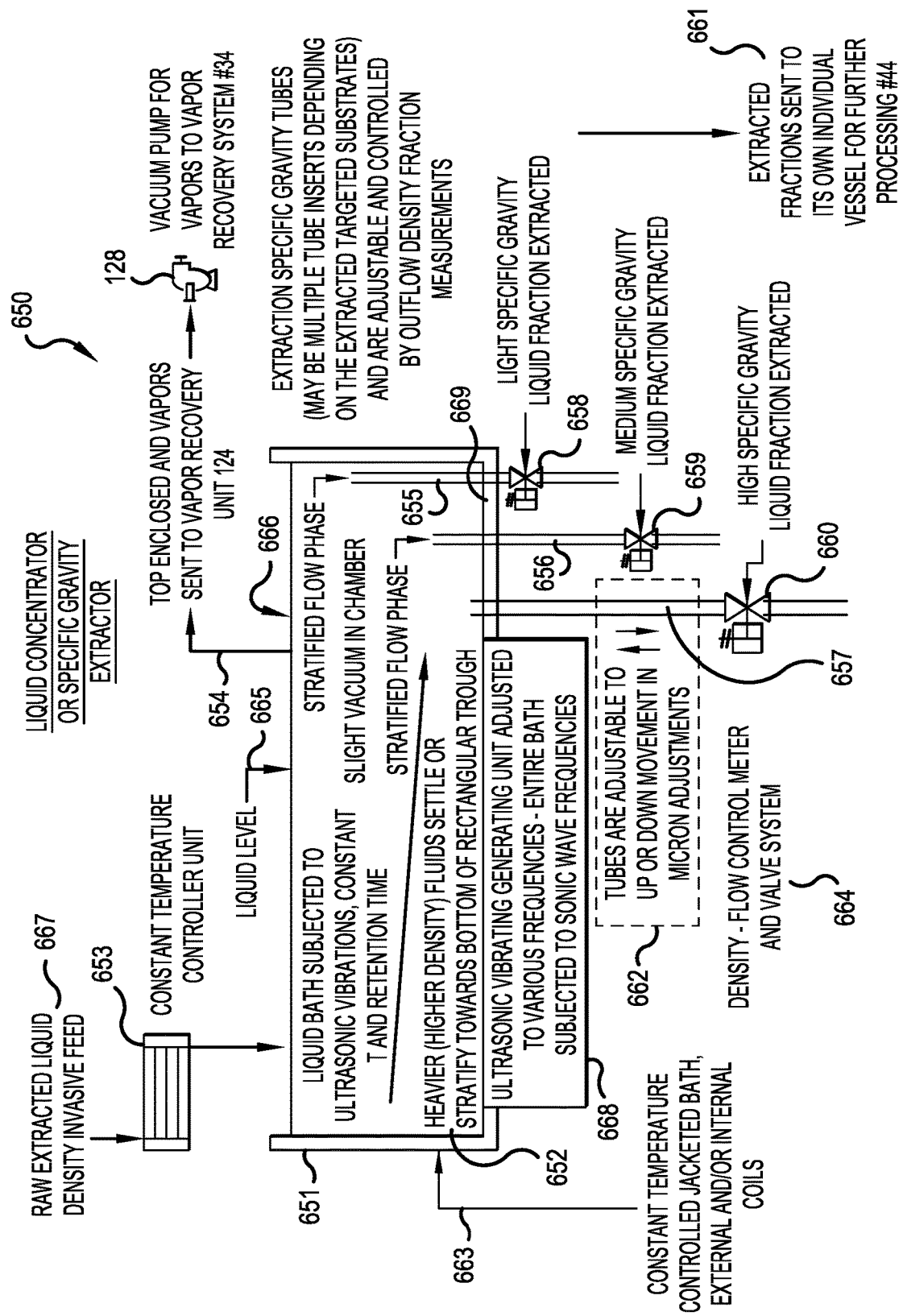
FIG. 6 is a schematic diagram, consistent with some embodiments, of a liquid concentrator or extractor. Shown are at least a bath with evacuation tubes for evacuating different liquids of different specific gravities.

Referencing FIG. 6, a simplified schematic drawing of an exemplary extractor 650 (also referred to as specific gravity extractor or a liquid concentrator) that may be used in operation 37 of FIG. 1E.

Exemplary extractor 650 includes a tank 651 (e.g., a rectangular trough) filled with a liquid 666 to water level 665. Raw extracted liquid density invasive feed 667 may be added to liquid with temperature of the feed 667 controlled by constant temperature controller unit 653 (e.g., with external or internal heated coils for maintaining constant temperature). An ultrasonic vibrating generating unit 668 produces ultrasonic vibrations of various frequencies. A specific retention time is used.

Referencing feature 663, the combination of the ultrasonic frequencies, the constant temperature, and the retention time result in a stratification of the liquid 666 into lighter and heavier liquids with different specific gravities. Heavier (higher density) liquids settle or stratify towards the bottom of tank 651.

In the particular exemplary extractor 650 showed, there are three submerged vertical drain pipes 655, 656, and 657 for draining liquids of different specific gravities. In the example shown drain pipe 655 is highest relative to floor 669 (for draining lightest specific gravity liquid), drain pipe 656 if of intermediate height relative to floor 669 (for draining moderate specific gravity liquid), and drain pipe 657 is of lowest height relative to floor 669 (for draining heavy specific gravity liquids). Referencing feature 662, each of drain pipes 655, 656, and 657 are of adjustable height (relative to floor 669 of tank 651 by moving up or down relative to floor 669) within a micron of height. Thus, extraction specific gravity tubes 655, 656, 657 (which may be multiple tube inserts depending on the extracted targeted substrates) are adjustable and controlled by outflow density fraction measurements.

Drain pipes 655, 656, and 657 are associated with valves 658, 659, and 660, respectively. That is, valve 658 is configured to extract light specific gravity liquid fractions from drain pipe 655. Valve 659 is configured to extract medium specific gravity liquid fractions from drain pipe 656. And valve 660 is configured to extract high specific gravity liquid fractions from drain pipe 657. Collectively, pipes 655-657 and valves 658-660 are referred to as density-flow control meter and valve system 664. The extracted liquid fractions from valves 658-660 are sent via individual vessel for further processing in, for example, one or more operations after operation 37 of process 100. Conveyance 661 is configured for sending extracted fractions to their own individual vessels for further processing, such as in operation 44 of FIG. 1D.

Exemplary extractor 650 includes an enclosure (not shown) to prevent escape of water vapors that evaporate from water 666 of tank 651. A pump 128 may provide suction to move the captured water vapors via conveyance 654 to a vapor recovery system (e.g., vapor recovery unit 125 of FIG. 1C).

VI. Process of Cell Fracture and Chemical Extraction-FIG. 7

Figure 7:
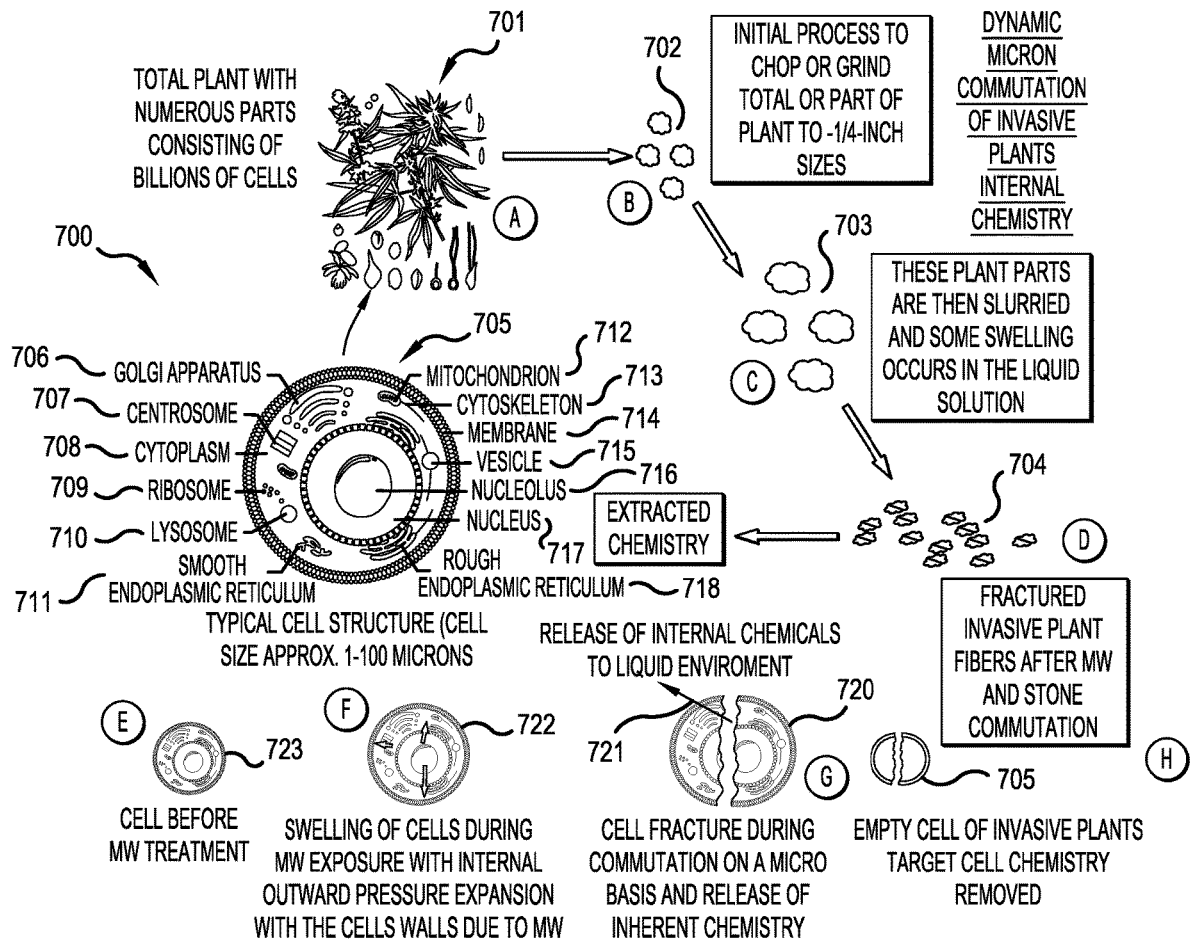
FIG. 7 is a process diagram, according to some embodiments, showing exemplary plant stock as it is processed according to some embodiments. Includes at least depiction of effects of wet-grinding and microwaving at a cellular level.

FIG. 7 illustrates a process 700 by which plant stock are processed, including processing by microwave treatment and stone commutation, to extract chemicals (e.g., oxalic acid and/or derivatives thereof) internal to the cells of the plant stock. That is, what occurs is a dynamic micron commutation of invasive plant's internal chemistry. Various stages (A-H) in the evolution of plant stock and plant cells are illustrated as they go through reduction, mixing into slurry, and processing by microwave treatment and stone commutation.

Referencing FIG. 7, at stage A, plant stock 701 is received consisting of billions of cells.

At stage B, plant stock 701 are chopped or ground (entire of part of plant) to yield plant pieces 702 of approximately ¼ inch in size.

At stage C, plant pieces 703 are transported.

At operation D, plant stock are mixed with water (or other carrier liquid) to form suspended plant particles 704.

The internal chemistry and typical cell structure of plant cell 705 (approximately 1-100 microns in size) is shown at stage E before microwave treatment and commutation. Plant cell structures include a golgi apparatus 706, a centrosome 707, cytoplasm 708, ribosome 709, lysosome 710, smooth endoplasmic reticulum 711, mitochondrion 712, cytoskeleton 713, membrane 714, vesicle 715, nucleolus 716, nucleus 717, and rough endoplasmic reticulum 718. At stage E as plant cell 723 is shown before microwave treatment.

At stage F, a swelling of a cell 722 is shown as swelling occurs during microwave exposure with internal outward pressure expansion.

At stage G, a cell fracture 720 occurs commutation on a micro basis and there is release of the inherent chemistry. That is a release of the internal chemicals 721 of the cell into the liquid environment.

At stage H, an empty cell 705 of an invasive target cell with internal chemistry removed is shown. What is left is fractured invasive plant fibers are microwave treatment and stone commutation.

VII. Graphs Illustrating Efficiencies of Microwave Treatment and Stone Commutation of Plant Cells-FIGS. 8-10

Figure 8:
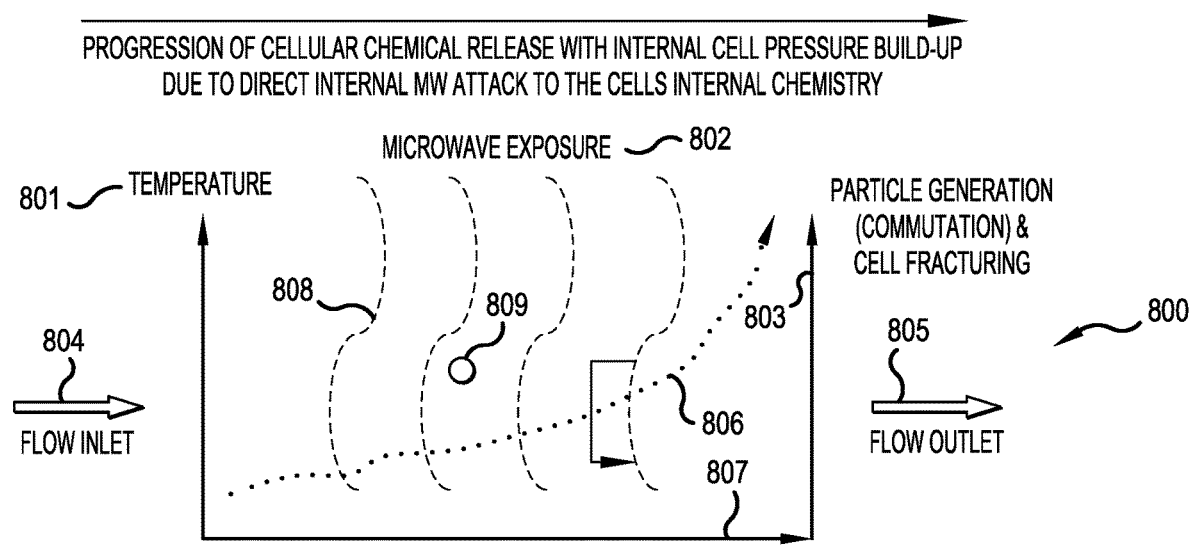
FIG. 8 is a graph, consistent with some embodiments, illustrating a progression of cellular chemical release with internal cell pressure build-up due, at least partly, to internal microwave attack to cell's internal chemistry.

Referencing FIG. 8, shown is an exemplary graph 800 illustrating a progression of cellular chemical release with internal cell pressure build-up due to direct internal microwave attack to the cell's internal chemistry.

Graph 800 includes a depiction of a flow 804 of slurry toward the microwave treatment and stone commutation operation and a flow outlet 805 after the outlet. Axis 801 (temperature) is vertical and increases upward relative to horizontal axis 807 (time). Axis 803 (extent of cell fracturing—from combination of cell swelling and stone commutation) also is vertical and increases upward relative to horizontal axis 807 (time). Also illustrated are microwave radiation waves 808 from microwave exposure 802 and plant cell 809 bombarded by the microwave radiation exposure 802.

Curve 806 illustrates the degree of chemical release of chemicals (e.g., oxalic acid) into a liquid environment. Curve 806 shows that the degree of chemical release is low near the intersection of axis 807 (time beginning), axis 801 (temperature low). Axis 803 (extent of cell fracturing) is also low. Curve 806 gradually increases showing release of internal cell chemistry and axis 807 (time), axis 801 (temperature), and axis 803 (degree of cell fracturing) all increase.

Thus, overall it is illustrated that as time increases, temperature increases from microwave exposure, and cell fracturing increases, the chemical release of a plant cell's internal chemistry nears 100%.

Figure 9:
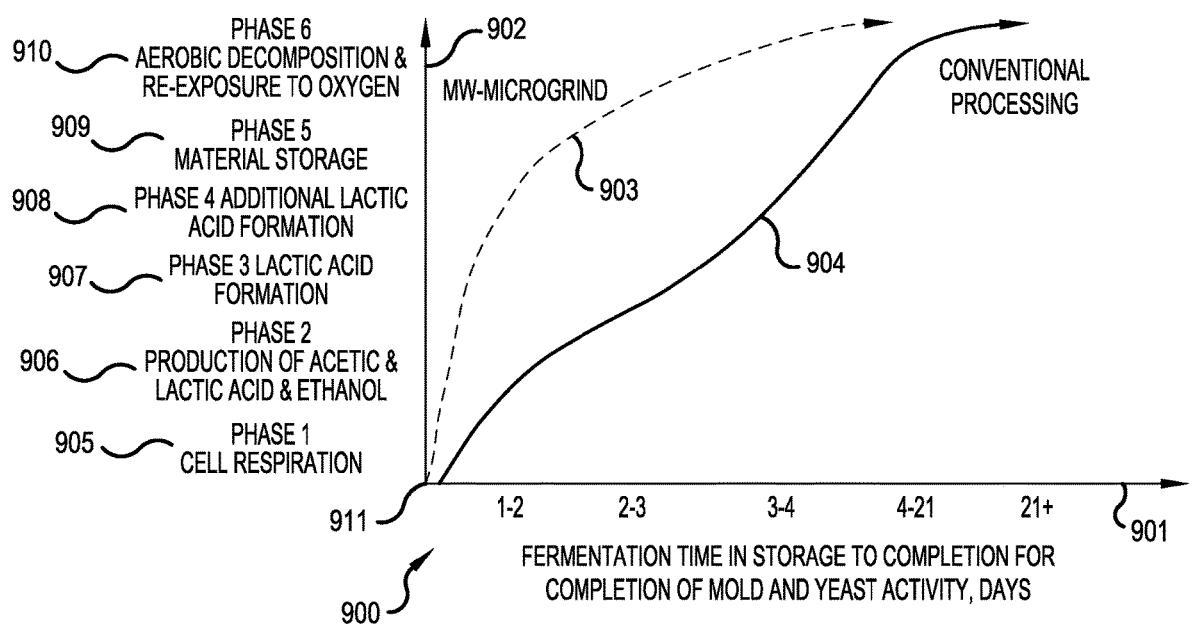
FIG. 9 is a graph, consistent with some embodiments, comparing an effect on a rate of cell aerobic decomposition dependent on whether processing is (a) with a combination of microwave treatment and micro-grinding or (b) with conventional processing.

Referencing FIG. 9, shown is a Graph 900 showing that a number of days needed for plant stocks to ferment is reduced for plant stock process with the described microwave treatment/stone commutation process versus the number of days needed for plant stocks to ferment with conventional processing. The fermentation discussed in this Graph 900 is related to silage production as discussed above relative to operation 68 of process 100.

Graph 900 includes an intersection 911 of a vertical axis 902 representing advancing phases 1 thru 6 (905-910) and of a horizontal axis 901 showing time measured in days. Curve 904 represents fermentation by conventional processing as the value in both axis 902 and 901 increase. Curve 903 represents fermentation after plant stock has been treated by microwave treatment/micro-grind (i.e., wet-grind).

Turning first to axis 902, the phases start towards the bottom of the axis with phase 1-cell respiration (item 905), then phase 2-production of acetic and lactic acid and ethanol (item 906), then phase 3-lactic acid formation (item 907), phase 4-additional lactic acid formation (item 908), phase 5-material storage (item 909), phase 6-aerobic decomposition and re-exposure to oxygen 910.

The pattern shown by Graph 900 is that curve 903 (wet fiber produced by microwave/micro-grind) rises faster than curve 904 (conventional processing). Thus, wet fiber that has been produced in part by microwave processing and micro-grinding ferments quicker and more efficiently that plant fibers processed through conventional processing.

Figure 10:
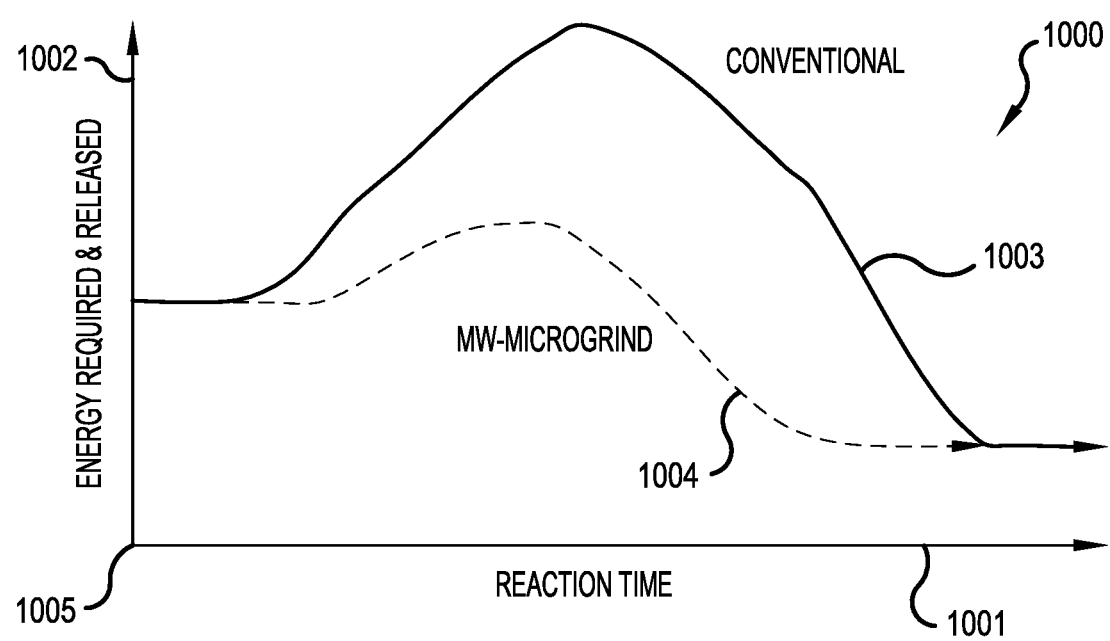
FIG. 10 is a graph, consistent with some embodiments, comparing energy usage and reaction time dependent on whether processing is (a) with a combination of microwave treatment and micro-grinding or (b) with conventional processing.

Referencing FIG. 10, a Graph 1000 illustrates how much energy is required over a span of reaction time for processing with microwave/micro-grind versus conventional processing. Graph illustrates that over a span of reaction time less energy is required and released by processing with microwave/micro-grind versus conventional processing.

Graph 1000 includes intersection 1005 of vertical axis 1002 representing increasing energy required and released and horizontal axis 1001 representing increasing reaction time. Solid curve 1003 represents energy required and released over time by conventional processing. Dotted curve 1004 represents energy required and released over time by microwave/micro-grind processing.

As can be seen, curve 1003 rises higher than curve 1004 representing greater energy required and released by conventional processing versus microwave/micro-grind processing.

Figure 11:
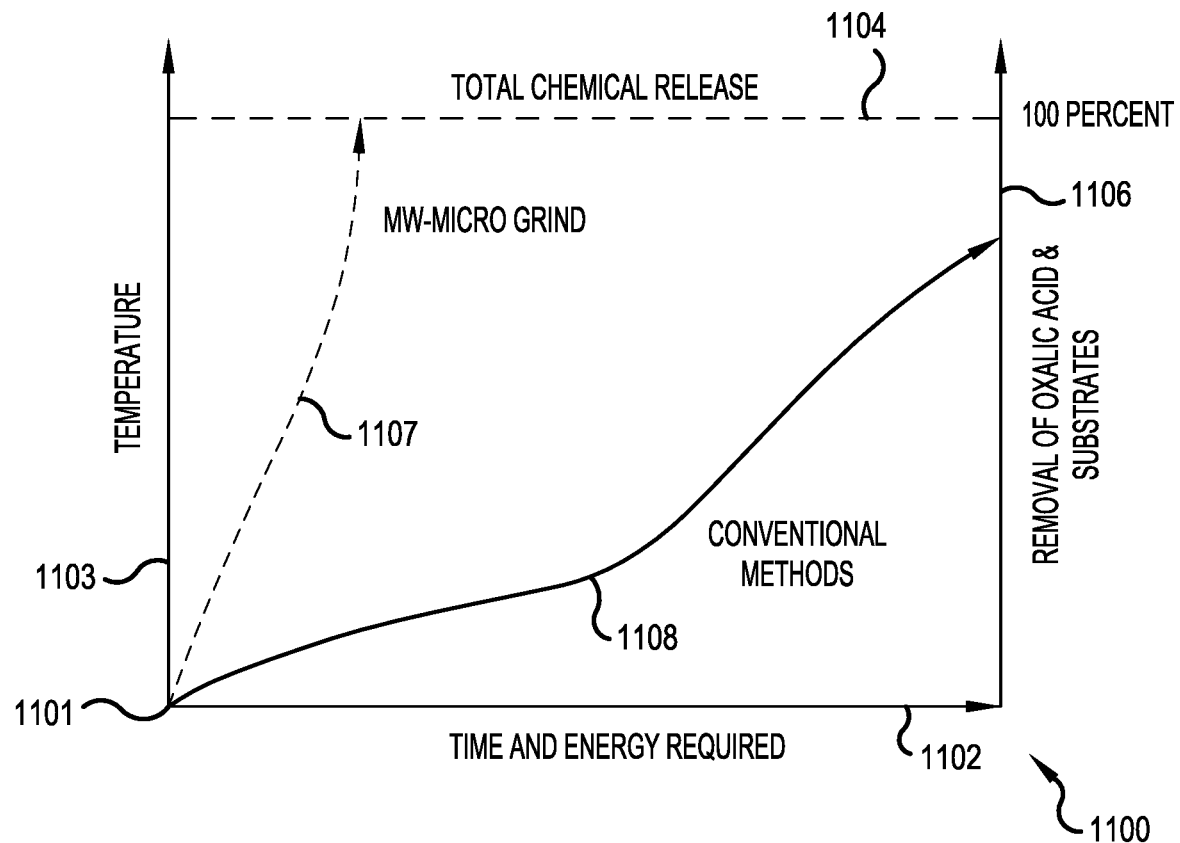
FIG. 11 is a graph, consistent with some embodiments, comparing time and energy to achieve total chemical release (of noxious chemicals) dependent on whether processing is (a) with a combination of microwave treatment and micro-grinding or (b) with conventional processing.

Referencing FIG. 11, a Graph 1100 illustrates how much time and energy is required to achieve 100% total chemical release of chemicals stored in plant cells for microwave/micro-grind processing versus conventional processing. Graph 1100 illustrates that much less time and energy is required to achieve 100% total chemical release of chemicals stored in plant cells for microwave/micro-grind processing as compared with conventional processing. Graph 1100 also illustrates that temperatures rise higher with microwave/micro-grind processing.

Graph 1100 illustrates intersection 1101 of vertical axis 1103 representing increasing temperature and horizontal axis 1102 representing increasing time and energy required. Horizontal axis 1102 also intersects vertical axis 1106 (parallel to axis 1103) representing increasing removal of oxalic acid and substrates. Dotted line 1104 which runs parallel to axis 1102 and perpendicular to axes 1103 and 1106 represents 100% total chemical release of chemicals (e.g., oxalic acid) from processed plant cells.

Dotted curve 1107 representing processing by microwave/micro-grind starts at intersection 1101 and rises to dotted line 1104, showing that processing by microwave/micro-grind achieves 100% chemical release. Solid curve 1108 representing conventional processing also starts at intersection 1101 and rises gradually toward, but does not reach, dotted line 1104-illustrating that it does not achieve 100% total chemical release. Moreover, solid curve 1108 consumes more of axis 1102 indicating it consumes more time and energy to achieve a lesser state of chemical release relative to microwave/micro-grind processing.

Thus, Graph 1100 illustrates that much less time and energy is required to achieve 100% total chemical release of chemicals stored in plant cells for microwave/micro-grind processing as compared with conventional processing. Graph 1100 also illustrates that temperatures rise higher with microwave/micro-grind processing.

VIII. Flow Charts Illustrating One or More Processes-FIGS. 12-17

Figure 12:
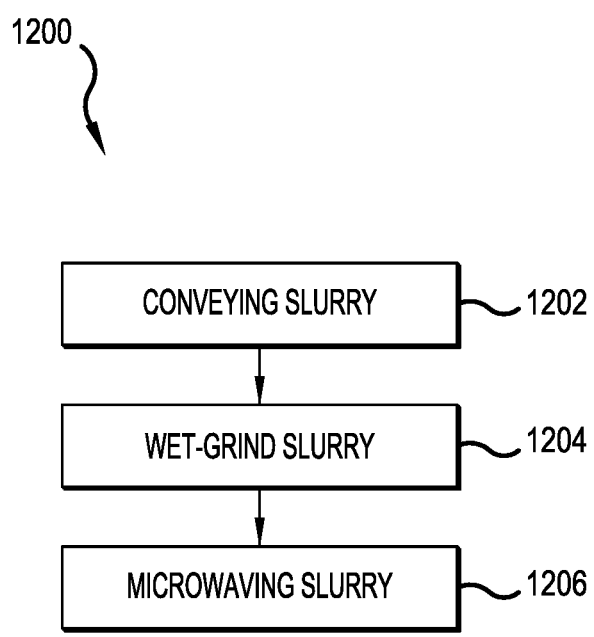
FIG. 12 is a flow diagram illustrating a method according to some embodiments.

FIG. 12 and the following figures include various examples of operational flows. Discussions and explanations may be provided with respect to the above-described principles, embodiments, and environments of FIGS. 1-11. However, the described operational flows may be executed and implemented in other environments and with different components.

In addition, although the various operational flows are presented in illustrated sequences, it should be understood that in various embodiments the various operations may be performed in different sequential orders other than those which are illustrated, or may be performed concurrently or simultaneously.

Further, in the following figures that depict various flow processes, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently. For additional clarity, some optional operations may be placed in broken line boxes.

FIG. 12 illustrates a method 1200 for extracting useful products from at least one of invasive, poisonous or toxic plant stock, may consistent with some embodiments, include one or more of operations 1202, 1204, and 1206. Collectively, operations 1202-1206 are at least similar to operation 21 of FIG. 1C.

Referencing FIG. 12, in some embodiments operation 1202 regarding conveying the slurry includes at least conveying a slurry that contains at least one or more carrier liquids and at least some plant stock suspended in the one or more carrier liquids, the conveying being performed at least in part with a fluid conveyance of a wet-grinding apparatus. In some embodiments, operation 1202 may be implemented with at least a wet-grinding apparatus (e.g., wet-grinding apparatus (e.g., wet-grinding apparatus 121 of FIGS. 1C, 201 of FIGS. 2, and/or 421 of FIG. 4) that includes at least a fluid conveyance (e.g., 205 of FIG. 2) configured for receive and direct a slurry that contains at least one or more carrier liquids and at least suspended plant stock suspended in the one or more carrier liquids.

Consistent with some embodiments, operation 1204 includes at least driving at least one rotor disk of a set of flat grinding disks of the wet-grinding apparatus with a motor drive operably coupled with a high torque motor, the driving causing the set of flat grinding disks to accept the slurry on one or more surfaces, to grind the suspended plant stock, and to discharge the slurry. In some embodiments, operation 1204 may be implemented with at least a wet-grinding apparatus (e.g., wet-grinding apparatus (e.g., wet-grinding apparatus of FIGS. 1C and 2 or 421 of FIG. 4) that includes at least a set of flat grinding disks (e.g., 217 of FIG. 2, 417 of FIG. 4) that include at least one rotor disk (e.g., 210, 410) that is operably coupled to be driven by the motor drive (e.g., motor drive 204 driven by high torque motor 221), the set configured, when the at least one rotor disk is driven by the motor drive, to accept the slurry from the fluid conveyance 205, to grind the suspended plant stock, and to discharge the slurry.

Consistent with some embodiments, operation 1206 includes at least emitting microwave radiation, with at least one microwave emitter, toward at least a portion of the slurry at least one of before, while, or after the suspended plant stock is ground by the wet-grinding apparatus. In some embodiments, operation 1204 may be implemented with at least a microwave unit (e.g., 220 of FIG. 2, and/or microwave units 120, 122) that includes at least one microwave emitter (e.g., 211, 311) configured to emit microwave radiation toward at least a portion of the slurry at least one of before, while, or after the slurry is ground by the wet-grinding apparatus (e.g., 121, 201, and/or 401).

Figure 13:
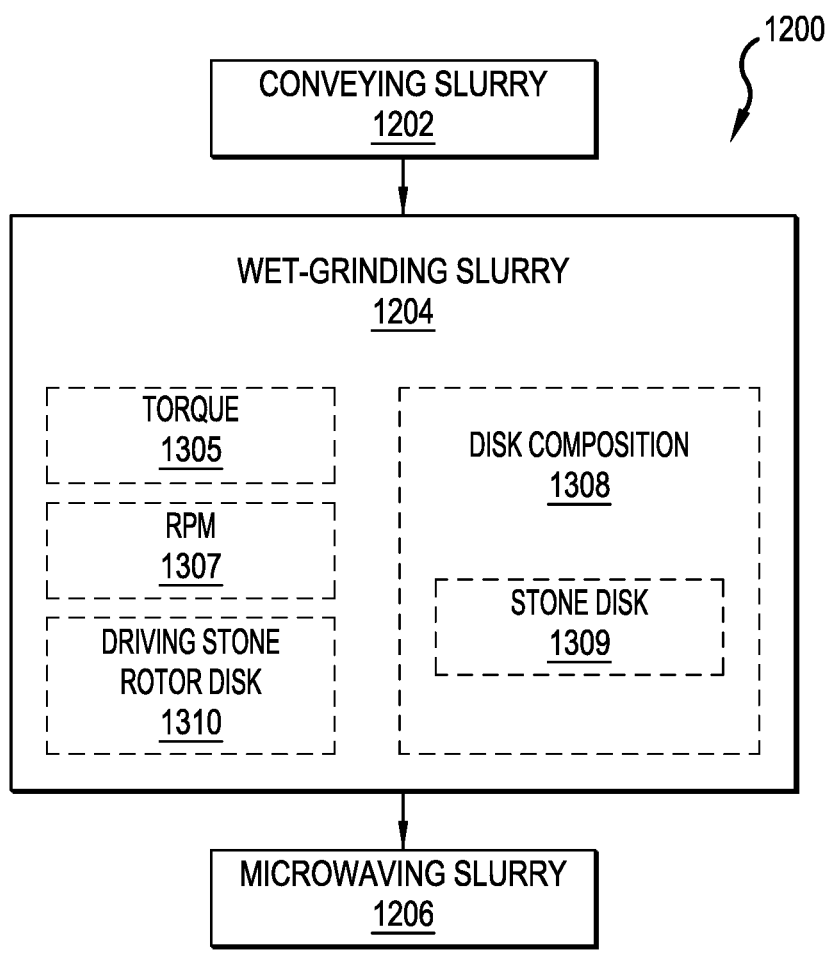
FIG. 13 is a flow diagram illustrating the method of claim 12, with additional optional embodiments.

Referencing FIG. 13, in some embodiments operation 1204 regarding wet-grinding the slurry optionally includes one or more of operations 1305, 1307, 1308, or 1310.

Consistent with some embodiments operation 1305 includes at least driving at least one rotor disk of a set of flat grinding stones with a motor drive operably coupled with a high torque motor at a torque in a range between 10.5 foot-pounds and 11,000 foot-pounds. In some embodiments operation 1305 is implemented at least with a high torque motor (e.g., 221) that is configured to provide torque in a range between 10.5 foot-pounds and 11,000 foot-pounds.

Consistent with some embodiments, operation 1307 includes at least driving at least one rotor disk of a set of flat grinding stones with a motor drive operably coupled with a high torque motor operating at between 60 rpm and 1,800 rpm. In some embodiments, operation 1307 is implemented at least with a high torque motor (e.g., 221) that is configured to operate at one or more speeds between 60 rpm and 1,800 rpm.

Consistent with some embodiments operation 1308 includes at least driving at least one rotor disk of a set of flat grinding disks that includes at least one of a stone disk, a steel alloy disc, or a disk composed in part of stone and in part of steel alloy. In some embodiments, operation 1308 is implemented at least in part with set of flat grinding disks (e.g., 217, 417) that includes at least one of a stone disk, a steel alloy disc, or a disk composed in part of stone and in part of steel alloy.

In some embodiments, operation 1308 optionally includes operation 1309.

Consistent with some embodiments, operation 1309 includes at least driving at least one rotor disk of a set of flat grinding disks that includes at least one flat grinding stone composed at least partly of at least one of silicon carbide, aluminum oxide, zirconia, or ceramic friable mixes. In some embodiments, operation 1309 is implemented at least with set of flat grinding disks (e.g. disks 210, 209 of set 217) includes at least one flat grinding disk composed at least partly of at least one of silicon carbide, aluminum oxide, zirconia, or ceramic friable mixes.

Consistent with some embodiments, operation 1310 includes at least driving at least one rotor stone of a set of flat grinding stones, the flat grinding stones including at least two stator stones and the at least one rotor stone, the individual flat grinding stones being aligned along respective axial holes about the motor drive, the driving including at least driving the at least one rotating stone with the high torque motor, the driving causing the slurry (1) to be received via the respective axially aligned holes from the fluid conveyance, (2) to be directed onto flat grinding surfaces of the individual flat grindings stones, (3) to be ground while the suspended plant stock is in solution in the slurry, and (4) to be discharged from outer perimeters defined by the individual flat grindings stones of the set of flat grinding stones. In some embodiments operation 1310 is implemented with at least a set of flat grinding stones (e.g., 217, 417), the set of flat grinding stones including at least two stator stones (e.g., 409A, 409B) and at least one rotor stone (e.g., 210, 410), the individual flat grinding stones being aligned along respective axial holes (e.g., 225) about the motor drive (e.g., 204, 404), the at least one rotor stone being configured to be driven by the high torque motor via the motor drive, and wherein when the at least one rotor stone is driven by the high torque motor the set of flat grinding stones is configured to receive the slurry via the respective axially aligned holes from the fluid conveyance, to direct slurry onto flat grinding surfaces (e.g., 226 of FIG. 2) of the individual flat grindings stones of the set, to grind the suspended plant stock while it is in solution in the slurry, and to discharge the slurry from outer perimeters (e.g., 227 of FIG. 2) defined by the individual flat grinding stones of the set of flat grinding stones.

Figure 14:
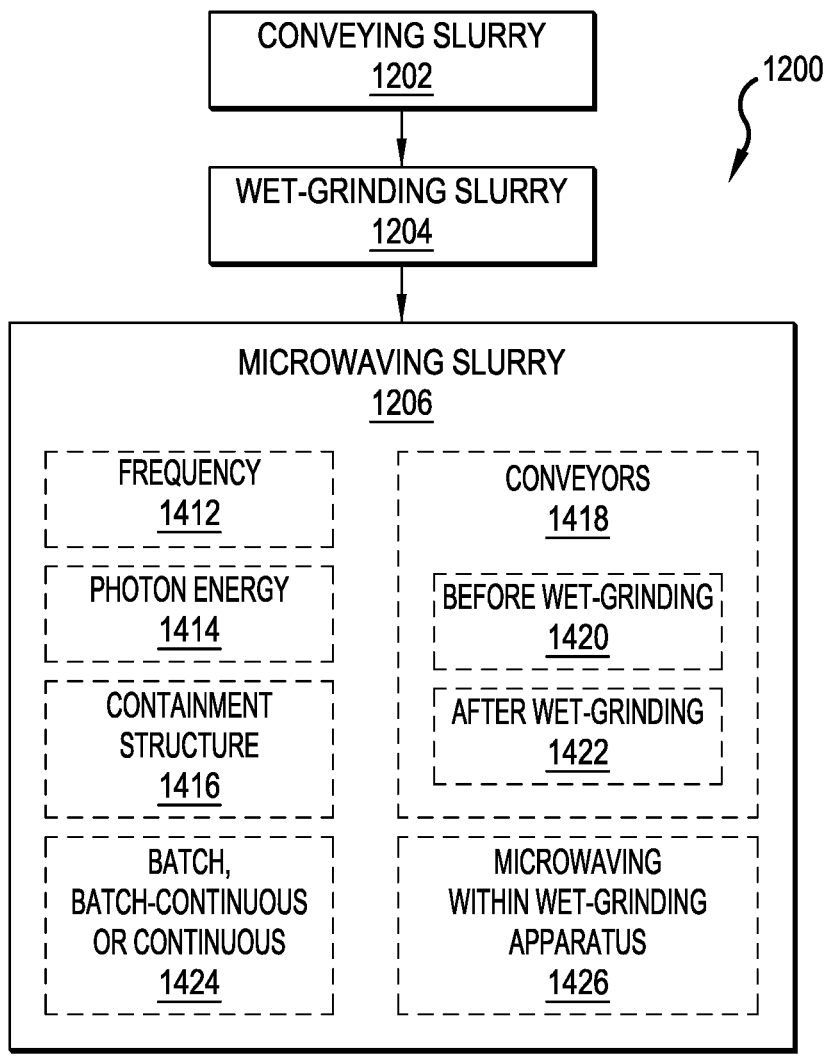
FIG. 14 is a flow diagram illustrating the method of claim 12, with additional optional embodiments.
Figure 15:
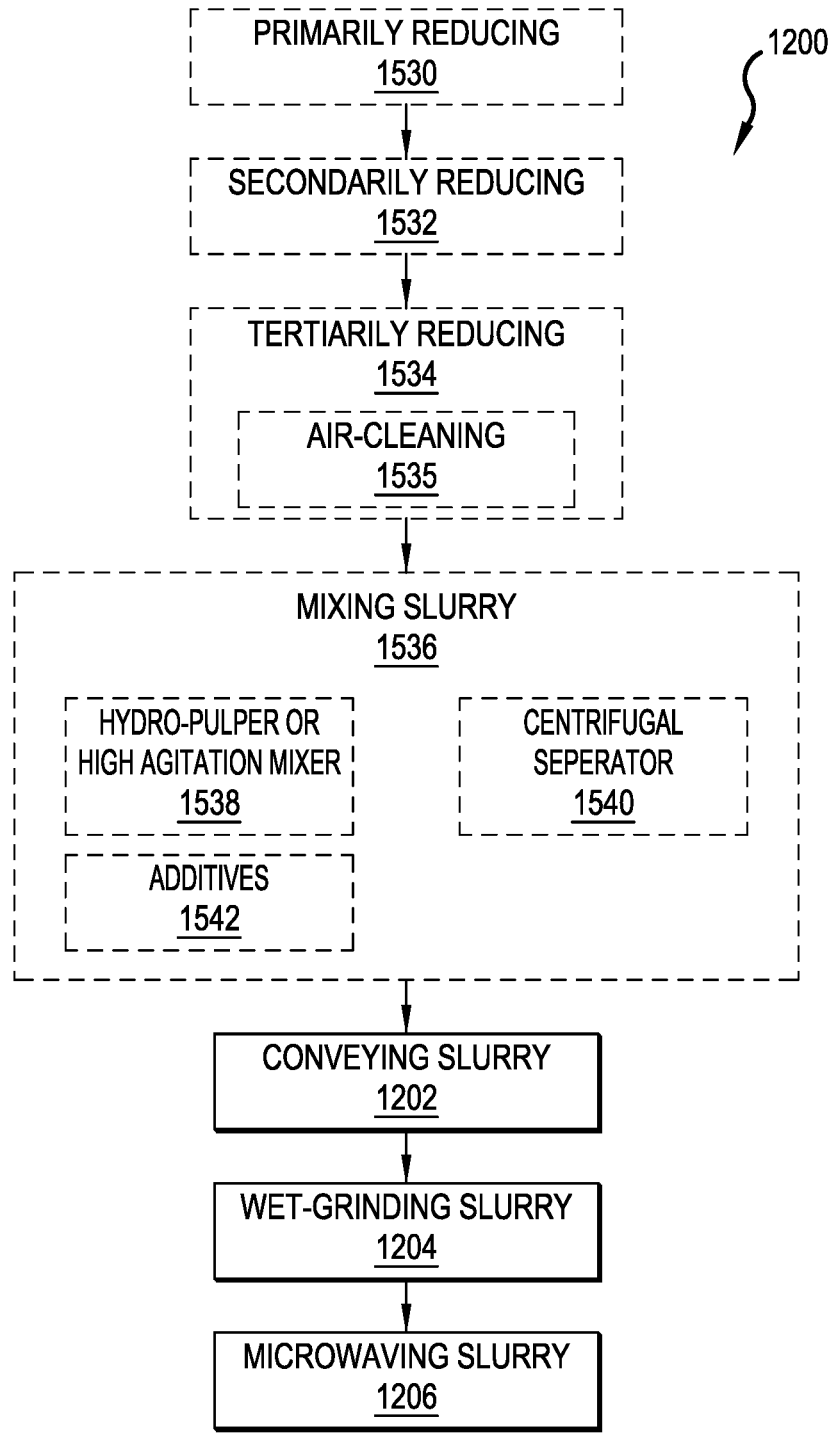
FIG. 15 is a flow diagram illustrating the method of claim 12, with additional optional embodiments.

Referencing FIG. 14, in some embodiments operation 1206 regarding microwaving the slurry optionally includes one or more of operations 1412, 1414, 1416, 1418, 1424 or 1426.

Consistent with some embodiments operation 1412 regarding microwaving the slurry includes at least emitting, with the at least one microwave emitter, at least some microwave radiation in a range between 300 GHz and 300 MHz. In some embodiments operation 1412 is implemented with at least at least one microwave emitter (e.g., 211, 411) is configured to emit at least some microwave radiation in a range between 300 GHz and 300 MHz.

Consistent with some embodiments operation 1414 regarding microwaving the slurry includes at least emitting, with the at least one microwave emitter, at least some microwave radiation with a photon energy between 1.24 to 1.24 micro electron volts. In some embodiments operation 1414 is implemented with at least at least one microwave emitter (e.g., 211, 411) is configured to emit at least some microwave radiation with a photon energy between 1.24 to 1.24 micro electron volts.

Consistent with some embodiments operation 1416 includes at least emitting the microwave radiation within a containment structure configured to contain the microwave radiation and gases off-gassed from the slurry during microwave radiation treatment, creating a negative atmosphere between 760 and 10-9 torr within the containment structure with a compressor, and converting the off-gassed gases to liquid form for capture with at least a vapor recovery unit that includes at least one condenser. In some embodiments operation 1416 is implemented at least with a microwave unit that includes at least a containment structure (e.g., 202 of FIGS. 2 and/or 313 of FIG. 3) configured to contain the microwave radiation and gases off-gassed from the slurry during microwave radiation treatment and a compressor (e.g., 223 of FIGS. 2 and/or 323 of FIG. 3) configured for creating a negative atmosphere between 760 and 10-9 torr in the containment structure. And operation 1415 being further implemented with a vapor recovery unit (e.g., 125) that includes at least one compressor for converting the off-gassed gases to liquid form for capture.

Consistent with some embodiments operation 1418 includes at least conveying the slurry through one or more high temperature-resistant conveyances that include at least one of tubes, coils, or troughs that are transparent to microwave radiation, and emitting, with the at least one microwave emitter, microwave radiation toward at least a portion of the one or more conveyances, wherein the emitting of microwave radiation causes cells of the ground plant stocks in the slurry within the one or more conveyances to expand thereby making a wet-grinding more effective. In some embodiments operation 1418 is implemented at least with a microwave unit (e.g., microwave unit 120 of FIG. 3) is separate from the wet-grinding apparatus and that includes at least one or more high temperature-resistant conveyances (e.g., 314) that include at least one of tubes, coils, or troughs that are transparent to microwave radiation and that are further configured for receiving and conveying the slurry and wherein the microwave emitter is positioned to emit microwave radiation (e.g., with microwave emitter 311 and Horn 312) toward at least a portion of the one or more conveyances, and wherein when the microwave emitter is in operation the emitted microwave radiation cause cells of the ground plant stocks within the one or more conveyances to expand thereby making a wet-grinding more effective.

In some embodiments, operation 1418 optionally includes one or more of operation 1420 or 1422.

Consistent with some embodiments operation 1420 includes at least emitting the microwave radiation toward at least the portion of the one or more conveyances before processing of the slurry in the wet-grinding apparatus and after the emitting of the microwave radiation, conveying the slurry, to an intake of the wet-grinding apparatus. In some embodiments operation 1420 is implemented with at least one or more one or more conveyances (314) that are configured to receive the slurry for exposure to the microwave radiation (e.g., from microwave emitter 311) before processing in the wet-grinding apparatus (e.g., 201 or 401) and are further configured to convey the slurry, after exposure to microwave radiation to the fluid conveyance (e.g., 205, 405) of the wet-grinding apparatus.

Consistent with some embodiments operation 1422 includes at least receiving the slurry in the one or more conveyances for exposure to microwave radiation after grinding in the wet-grinding apparatus and emitting the microwave radiation toward at least the portion of the one or more conveyances. In some embodiments operation 1422 is implemented with at least one or more conveyances (314) are configured to receive the slurry for exposure to the microwave radiation after grinding in the wet-grinding apparatus (e.g., 201 or 401).

Consistent with some embodiments operation 1424 includes at least emitting microwave radiation, with at least one microwave emitter of a microwave unit that is operating in at least one of a batch, batch-continuous or a continuous operation mode. In some embodiments operation 1424 is implemented at least with a microwave unit (e.g., 120 or 220) that is configured to operate in at least one of a batch, batch-continuous or a continuous operation mode.

Consistent with some embodiments operation 1426 includes at least emitting the microwave radiation toward the slurry while the slurry is at least partially within the wet-grinding apparatus, the wet-grinding apparatus being encased in an encasement configured for containing the microwave radiation and wherein the emitting of the microwave radiation toward the slurry causes cell fibers within the slurry to expand and thereby increase an effectiveness of grinding. In some embodiments operation 1426 is implemented with at least microwave unit (e.g., unit 220 of FIG. 2) is at least partially integrated as a portion of the wet-grinding apparatus (e.g., 201), the microwave unit including at least a the microwave emitter (211) configured to emit microwave radiation toward the slurry and an encasement (202) configured to encase the wet-grinding apparatus during microwave emissions and wherein the microwave radiation causes cell fibers within the slurry to expand and thereby increasing effectiveness of grinding.

Referencing FIGS. 15A and 15B, in some embodiments method 1200 optionally further includes one or more of additional operations 1530, 1532, 1534, or 1536.

Consistent with some embodiments operation 1530 includes at least primarily reducing a volume of plant stock by at least one of shredding or chopping the plant stock into pieces of less than 6 inches in length.

Consistent with some embodiments operation 1532 includes at least secondarily reducing a volume of plant stock that has previously undergone primary reduction by at least one of shredding or compacting the plant stock with at least one of a rotary shear, a compactor, or a hammer mill. In some embodiments operation 1532 is implemented at least with secondary reducing equipment (e.g., 107 of FIG. 1A), including at least one of a rotary shear a compactor, or a hammer mill, configured to at least one of shred or compact plant stock that has previously undergone primary reduction, thereby reducing its volume to produce compacted plant stock for transport.

Consistent with some embodiments operation 1534 includes at least tertiarily reducing plant stock with at least one of a granulator, a grinder, or a knife mill to further reduce secondarily reduced plant stock to reduce the plant stock to a particle size adapted for wet-grinding with wet-grinding apparatus. In some embodiments operation 1534 is implemented at least with tertiary reducing equipment (e.g., 111 of FIG. 1A), including at least one of a granulator, a grinder, or a knife mill, configured for further reducing secondarily reduced plant stock to render plant stock to a particle size adapted for wet-grinding with wet-grinding apparatus.

In some embodiments, operation 1534 optionally includes operation 1535.

Consistent with some embodiments operation 1535 includes at least capturing air-suspended particles escaping from tertiary reduction of plant stock with at least one of a cyclone or a baghouse. In some embodiments operation 1535 is implemented with at least air-cleaning system (e.g., 112 of FIG. 1A) configured to capture air-suspended particles escaping from tertiary reduction of plant stock, the air-cleaning system including at least one of a cyclone or a baghouse.

Consistent with some embodiments operation 1536 includes at least receiving the one or more carrier liquids and reduced plant stock in one or more containers and mixing said one or more carrier liquids and reduced plant stock in said one or more containers to form a slurry of which the suspended plant stock is between 1% and 25% by weight. In some embodiments operation 1536 may be implemented with at least a mixing apparatus (115 of FIG. 1B—e.g., hydra-pulper or high agitation mixer) configured for receiving the one or more carrier liquids and reduced plant stock in one or more containers and is further configured for mixing said one or more carrier liquids and the reduced plant stock in said one or more containers to form a slurry of which suspended plant stock is between 1% and 25% by weight.

In some embodiments, operation 1536 optionally includes one or more of operations 1538, 1540, or 1542.

Consistent with some embodiments operation 1538 includes at least mixing said one or more carrier liquids and reduced plant stock with at least one of a hydro-pulper or a high-agitation mixer. In some embodiments operation 1538 may be implemented with at least a mixing apparatus (e.g., 115) that includes at least one or a hydro-pulper or a high-agitation mixer for performing at least a portion of the mixing.

Consistent with some embodiments operation 1540 includes at least at least partially separating, with a centrifugal separator, at least one of earthly inerts or non-plant materials from the slurry. In some embodiments operation 1540 may be implemented with at least a mixing apparatus (e.g., 115) that further includes at least a centrifugal separator configured for at least partially separating at least one of earthly inerts or non-plant materials from the slurry.

Consistent with some embodiments operation 1542 includes at least mixing into at least one of the one or more carrier liquids or the slurry at least one of a surfactant, an additive, vegetation containing sugars, or an amylase type additive. In some embodiments operation 1542 may be implemented with at least a mixing apparatus (115) is further configured to receive and to mix into at least one of the one or more carrier liquids or the slurry at least one of a surfactant, an additive, vegetation containing sugars, or an amylase type additive.

Figure 16:
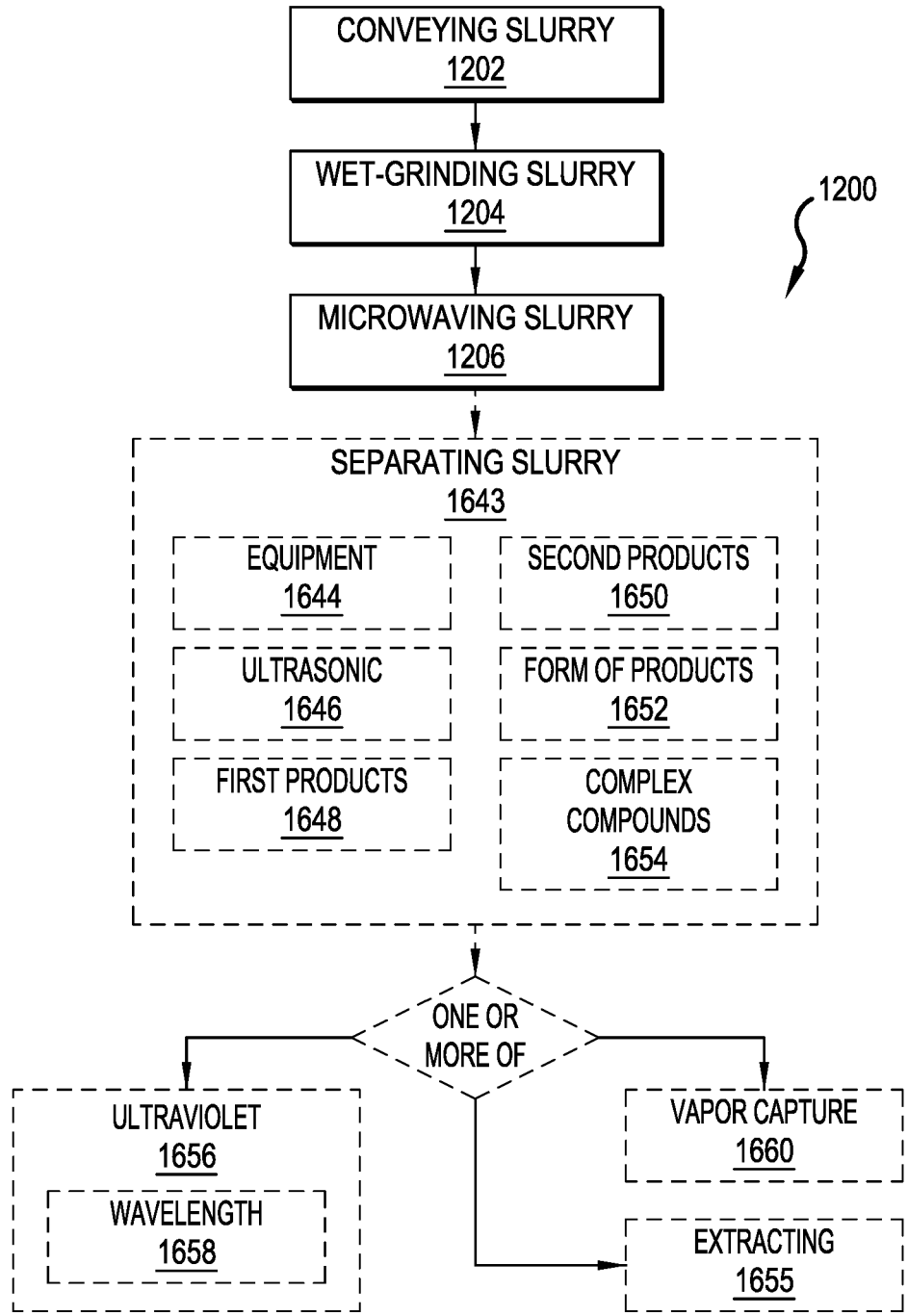
FIG. 16 is a flow diagram illustrating the method of claim 12, with additional optional embodiments.

Referencing FIG. 16, in some embodiments method 1200 optionally further includes one or more of additional operations 1643, 1655, 1656, or 1660.

Consistent with some embodiments operation 1643 includes at least separating the slurry into (1) a wet fiber suitable for further processing into one or more first products and (2) a liquid fraction suitable for further processing into one or more second products. In some embodiments operation 1643 may be implemented with at least a separator apparatus (130 of FIG. 1D—e.g., one or more of a decanter, a basket centrifuge, or an SS Buchner funnel system) configured to separate the slurry into a wet fiber suitable for further processing into one or more first products and a liquid fraction suitable for further processing into one or more second products.

In some embodiments operation 1643 optionally includes one or more of operations 1644, 1646, 1648, 1650, 1652, or 1654.

Consistent with some embodiments operation 1644 includes at least separating the slurry at least in part with a separator apparatus that includes at least one of a decanting centrifuge, a basket centrifuge, or an SS Buchner Funnel method. In some embodiments operation 1644 may be implemented with at least a separator apparatus (e.g., 130) includes at least one of a decanting centrifuge, a basket centrifuge, or an SS Buchner Funnel system.

Consistent with some embodiments operation 1646 includes at least directing ultrasonic waves having a frequency between 20 Hz and 200 Mhz toward the slurry, wherein the ultrasonic waves aid separation of the slurry into the liquid fraction and the wet fiber. In some embodiments operation 1646 may be implemented with at least an ultrasonic emitter (e.g., where separator apparatus 130 includes an ultrasonic emitter) configured to direct ultrasonic waves having a frequency between 20 Hz and 200 Mhz toward the slurry, wherein the ultrasonic waves aid separation of the slurry in the liquid fraction and the wet fiber.

Consistent with some embodiments operation 1648 includes at least separating the slurry into a wet fiber suitable for further processing into one or more first products that include at least one of gluten-free flour, pellets for agricultural feed, fillers for foodstuffs, plastics, adhesives, ethanol, or distilled spirits. In some embodiments operation 1648 may be implemented with at least a separator apparatus (e.g., 130) configured to separate the slurry into a wet fiber suitable for further processing into one or more first products that include at least one of gluten-free flour (e.g., 160), pellets for agricultural feed (e.g., 161), fillers for foodstuffs, plastics, adhesives, ethanol (e.g., 146), or distilled spirits (e.g., 147).

Consistent with some embodiments operation 1650 includes at least separating the slurry into a liquid fraction suitable for further processing into one or more second products that include at least one of a pesticide, an insecticide or a fungicide. In some embodiments operation 1650 may be implemented with at least a separator apparatus (e.g. 130) configured to separate the slurry into a liquid fraction suitable for further processing into one or more second products that include at least one of a pesticide, an insecticide or a fungicide (e.g., liquids 141 of FIG. 1F).

Consistent with some embodiments operation 1652 includes at least separating the slurry into a wet fiber suitable for further processing into at least one of liquid, solid, crystal, powdery, granular, or oily products. In some embodiments operation 1652 may be implemented with at least a separator apparatus (e.g. 130) configured to separate the slurry into a liquid fraction and a wet fiber that are suitable for further processing into one or more products that include at least one of liquid (e.g., 141, 146, 147), solid (141), crystal (141), powdery (161), granular, or oily (141) products.

Consistent with some embodiments operation 1654 includes at least separating the slurry into a wet fiber suitable for further processing into one or more materials that can be blended with at least one of an organic material, a dry material, a wet material, or a liquid to produce one or more complex compounds. In some embodiments operation 1654 may be implemented with at least a separator apparatus (e.g. 130) configured to separate the slurry into a liquid fraction and a wet fiber that are suitable for further processing into one or more products that can be blended with at least one of an organic material, a dry material, a wet material, or a liquid to produce one or more complex compounds.

As discussed above relative to FIG. 16, in some embodiments method 1200 may optionally include one or more of additional operations 1655, 1656, or 1660.

In some embodiments operation 1655 includes at least extracting at least one of an oxalic acid fraction, an oxalic salt fraction, or organic compounds from the liquid fraction with at least one of ultrasonic settling, centrifuging, or liquid-liquid separation. In some embodiments operation 1655 may be implemented with at least an extractor (e.g., 137, and/or extractor 650) that is configured to accept the liquid fraction separated by the separator apparatus and extract at least one of an oxalic acid fraction, an oxalic salt fraction, or organic compounds from the liquid fraction with at least one of ultrasonic setting, centrifuging, or liquid-liquid separation.

In some embodiments operation 1656 includes at least directing germicidal ultraviolet light radiation toward at least one of the slurry, the liquid fraction or the wet fiber, wherein the ultraviolet light is configured to reduce a risk of at least one of bacterial or fungal growth. In some embodiments operation 1656 is implemented with at least an ultraviolet light chamber (e.g., 131 and/or 154 of FIG. 1D) configured with an ultraviolet emitter (not shown) for directing germicidal ultraviolet light radiation toward at least one of the slurry, the liquid fraction or the wet fiber, wherein the ultraviolet light is configured to reduce a risk of at least one of bacterial or fungal growth.

Further referencing FIG. 16, in some embodiments operation 1656 optionally includes operation 1658).

Consistent with some embodiments operation 1658 includes at least directing at least some ultraviolet waves of the ultraviolet light waves that have one or more wave lengths in a range between 100 and 2809 nanometers. In some embodiments operation 1658 is implemented with at least an ultraviolet light chamber (e.g., 131 and/or 154 of FIG. 1D) configured with an ultraviolet emitter (not shown) for directing at least some ultraviolet waves of the ultraviolet light waves that have one or more wave lengths in a range between 100 and 2809 nanometers.

Consistent with some embodiments operation 1660 includes at least creating a negative atmosphere in one or more chambers containing at least some of the slurry to facilitate capture of at least some light volatiles escaping from at least one of the slurry or the extracted liquid fraction and converting at least some of the captured light volatiles into one or more liquid forms. In some embodiments operation 1660 may be implemented with at least a vapor recovery unit (e.g., 125 of FIG. 1C) that includes at least one or more conveyances for conveying off-gassed vapors escaping from at least one of the slurry or the liquid fraction and a compressor configured to receive the off-gassed vapors from the one or more conveyances and to convert the off-gassed vapors into one or more liquid forms.

It is noted that in some embodiments of at least one of an invasive, a poisonous or a toxic plant stock includes at least one of tumbleweed (salsula targus), kudzu, rosemary bean (*Abrus precatorius*) or sage brush plant stock.

Figure 17:
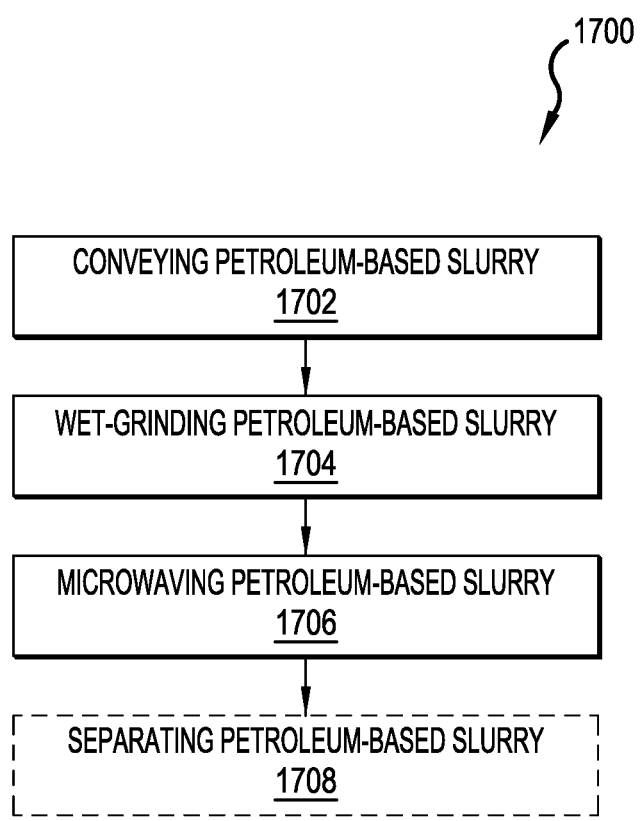
FIG. 17 is a flow diagram illustrating a method according to some embodiments.

FIG. 17 is an flow chart illustrating an exemplary method 1700 for extracting useful products from petroleum reservoir materials. Consistent with some embodiments method 1700 includes operations 1702, 1704, 1706 and optionally operation 1708. It is noted that these operations may be implement with at least some of the equipment discussed above relative to method 1200.

Consistent with some embodiments operation 1702 includes at least conveying a slurry that contains at least one or more carrier liquids and at least some petroleum-reservoir materials suspended in the one or more carrier liquids, the conveying being performed at least in part with a fluid conveyance of a wet-grinding apparatus. In some embodiments operation 1702 may be implemented with at least a wet-grinding apparatus (e.g., 201 of FIGS. 2 and/or 401 of FIG. 4) that includes at least a fluid conveyance (e.g., 205 of FIG. 2) configured for receive and direct a slurry that contains at least one or more carrier liquids and at least some petroleum-reservoir materials suspended in the one or more carrier liquids.

Consistent with some embodiments operation 1704 includes at least driving at least one rotor disk of a set of flat grinding disks of the wet-grinding apparatus with a motor drive coupled with a high torque motor, the driving causing the set of flat grinding disks to accept the slurry onto one or more grinding surfaces of individual grinding disks of the set of flat grinding disks, to grind the suspended petroleum-based reservoir materials, and to discharge the slurry. In some embodiments operation 1704 may be implemented with at least a wet-grinding apparatus (e.g., 201 of FIGS. 2 and/or 401 of FIG. 4) that includes at least a high torque motor, a motor drive operably coupled to be driven by the high torque motor, and a set (e.g., 217 of FIGS. 2 and/or 417 of FIG. 4) of flat grinding disks that include at least one rotor disk (e.g., 210 and/or 410) that is operably coupled to be driven by the motor drive (e.g., motor drive 204 driven by high torque motor 221), the set configured, when the at least one rotor disk is driven by the motor drive, to accept the slurry from the fluid conveyance, to grind the suspended petroleum-reservoir materials, and to discharge the slurry.

Consistent with some embodiments operation 1706 includes at least emitting microwave radiation, with at least one microwave emitter, toward at least a portion of the slurry at least one of before, while, or after the suspended petroleum-reservoir materials are ground by the wet-grinding apparatus. In some embodiments operation 1706 may be implemented with at least a microwave unit (e.g., 220 of FIG. 2, and/or microwave units 120, 122) that includes at least one microwave emitter (e.g., 211, 311) configured to emit microwave radiation toward at least a portion of the slurry at least one of before, while, or after the slurry is ground by the wet-grinding apparatus (e.g., 121, 201, and/or 401).

Optionally, method 1700 includes operation 1708, includes at least separating the slurry into (1) a solid residue and (2) a petroleum liquid fraction suitable for further processing into one or more petroleum-based products. This operation is performed with separator apparatus 130 (e.g. one or more of a decanter, a basket centrifuge, or an SS Buchner funnel system).

In addition to the above disclosure, the following discussion is provided:

1. The additives for pharmaceuticals and supplements either whole or partial.
2. Derivatives from invasive plants discussed in this document could be excellent surfactants or cleaners for many various types of metals and nonmetals. Potential uses include for electronics, chemical plants, normal household usage, and commercial and industrial applications.
3. These derivatives could also be used for biological control services or for an aerosol, or liquid for controlling various vectors such as bacteria and microbes. The derivatives may be very effective in controlling or eliminating germs such as corona type viruses. Many other unexplored and new biological germs may not yet discovered.
4. Kudzu is an invasive plant brought here by the Corps of Engineers to help erosion control. It has gotten wildly out of control but can be an excellent source of food. It has inherent derivatives for use in many products. Therefore, harvesting this plant under controlled conditions provides an economical food source. It could also be useful as application as a filler in commercial, agricultural, pharmacal and industrial products.
5. Reference is made to Toxic Plants of North America, Second Edition by George E Burrows and Ronald J. Tyrl, which describes many plants that present opportunities in the medical and chemical fields, along with their derivatives.
6. Plants such as the very poisonous variety, may be excellent for controlling certain diseases in a natural manner and not synthetically derived. These plants could be used as a supplement or as an additive to existing chemicals to achieve a higher in purpose of effectiveness. Additionally, these invasive plants may have a great value, being naturally occurring, with shorter half-lives and therefore not remaining in the environment.
7. It may be desirable to separate the various parts of the plants such as the leaves, the stems or the flowers for higher benefits for various applications. Example is the Roseberry bean (arbus *precatorius*) is known to kill some plants that may be undesirable or noxious. It may be an excellent replacement for commercial week-killers that are derived from synthetically-derived chemicals.
8. It is noted that in some embodiments the MW-micro grind systems herein described can be a plurality of machines operating in series or in parallel depending or both on the circumstances of the materials being processed. Additionally, the feedstock or slurry being may be recycled back through a process at certain points to for production of certain products. Combinations of various types of plants may be processed at the same time.
9. The plants described in this document generally have extensive chemical complexes that are not easily synthesized in the lab. Therefore, the systems and processes described in this document provide plant-derived products with superior properties as compared with synthetically derived chemicals, providing potential for applications in the medical industrial and commercial fields.
10. Plants such as those described in this document can have significant derivatives and substrates for products such as plastics, textiles, binders for construction, glues or adhesives etc.
11. Unlike the other technologies, the microwave and micro-grind technologies described herein preserve a plants composite composition. They allow for removal of portions such as the fibers that can be effective and useful for use as a food application or other applications.
12. Processes described herein allow for reprocessing the end products to produce more affective products. For example, fiber remaining from the extracted plant could be re-processed to another form or treated in a different manner.
13. Upon receiving plants at a processing site, they may be enclosed in a contained area and treated with various gases, ultraviolet light or microwaves to enhance their prepare the for further processing according to operations described herein.
14. It should be noted that when a mixture of some plant-derived, prepared solutions, are allowed to stand for extended an extended period of time, this may cause the overall mixture to form molds that may have very excellent properties for many applications.
15. When preparing a solution not using a grind process and only using extreme heat over a prolonged time, it has been found that this may cause the solution to lose many of its inherent properties due to excessive heat and time.
16. At operation 5 of FIG. 1A, the plant feed stock can be stored and prepared in a gaseous or spray atmosphere to enhance the overall efficiency of method 100. The gases used may include oxygen, nitrogen, or other prepared gases and spray ingredients, such as acids, caustic substances, to nutrients or extracts from the process.
17. At operation 21, the refined material can be processed in parallel or series and/or recycled for reprocessing during the micro-grinding or shearing process.
18. At operation 30, there are many types of fluid separators for separating solids to liquid.
19. At operation 37, various separating equipment devices can be employed depending on the material(s) being processed and many types of light sources or gravitational instruments can be employed.

It will be understood by those skilled in the art that the terminology used in this specification and in the claims is "open" in the sense that the terminology is open to additional elements not enumerated. For example, the words "includes" should be interpreted to mean "including at least" and so on. Even if "includes at least" is used sometimes and "includes" is used other times, the meaning is the same: includes at least. In addition, articles such as "a" or "the" should be interpreted as not referring to a specific number, such as one, unless explicitly indicated. At times a convention of "at least one of A, B, or C" is used, the intent is that this language includes any of A alone, B alone, C alone, A and B, B and C, A and C, all of A, B, and C, or any combination thereof. The same is indicated by the conventions "one of more of A, B, or C." Similarly, the phrase "A, B, and/or C" is intended to include any of A alone, B alone, C alone, A and B, B and C, A and C, all of A, B, and C or any combination thereof.

And as previously indicated elements, components, or operations should not be regarded as essential unless they are so explicitly described. The teachings contained herein may be adapted to a variety of embodiments arranged and composed in a wide variety of ways.

The above description of various embodiments is intended to be illustrative not exhaustive and is not intended to limit this disclosure, its application, or uses. Those skilled in the art will be able to imagine embodiments not described but that are consistent with the principles and teachings described herein. Therefore, the above description of exemplary embodiments is not intended to limit the scope of this disclosure, which should be defined only in accordance with the following claims and equivalents thereof.

I claim:

1. A method for extracting useful products from at least one of invasive, poisonous or toxic plant stock, the method comprising:
   conveying a slurry that contains at least one or more carrier liquids and at least some plant stock suspended in the one or more carrier liquids, the conveying being performed at least in part with a fluid conveyance of a wet-grinding apparatus;
   driving at least one rotor disk of a set of flat grinding disks of the wet-grinding apparatus with a motor drive operably coupled with a high torque motor, the driving causing the set of flat grinding disks to accept the slurry on one or more surfaces, to grind the suspended plant stock, and to discharge the slurry; and
   emitting microwave radiation, with at least one microwave emitter, toward at least a portion of the slurry while, the suspended plant stock is ground by the wet-grinding apparatus.

2. The method of claim 1, wherein the driving at least one rotor disk of a set of flat grinding disks of the wet-grinding apparatus with a motor drive operably coupled with a high torque motor comprises:
   driving at least one rotor disk of a set of flat grinding stones with a motor drive operably coupled with a high torque motor at a torque in a range between 10.5 foot-pounds and 11,000 foot-pounds.

3. The method of claim 1, wherein the driving at least one rotor disk of a set of flat grinding disks of the wet-grinding apparatus with a motor drive operably coupled with a high torque motor comprises:
   driving at least one rotor disk of a set of flat grinding stones with a motor drive operably coupled with a high torque motor operating at between 60 rpm and 1,800 rpm.

4. The method of claim 1, wherein the driving at least one rotor disk of a set of flat grinding disks of the wet-grinding apparatus with a motor drive operably coupled with a high torque motor comprises:
   driving at least one rotor disk of a set of flat grinding disks that includes at least one of a stone disk, a steel alloy disc, or a disk composed in part of stone and in part of steel alloy.

5. The method of claim 4, wherein the driving at least one rotor disk of a set of flat grinding disks that includes at least one of a stone disk, a steel alloy disc, or a disk composed in part of stone and in part of steel alloy comprises:
   driving at least one rotor disk of a set of flat grinding disks that includes at least one flat grinding stone composed at least partly of at least one of silicon carbide, aluminum oxide, zirconia, or ceramic friable mixes.

6. The method of claim 2, wherein the driving at least one rotor disk of a set of flat grinding disks of the wet-grinding apparatus with a motor drive operably coupled with a high torque motor, the driving causing the set of flat grinding disks to accept the slurry on one or more surfaces, to grind the suspended plant stock, and to discharge the slurry comprises:
   driving at least one rotor stone of a set of flat grinding stones, the flat grinding stones including at least two stator stones and the at least one rotor stone, the individual flat grinding stones being aligned along respective axial holes about the motor drive, the driving including at least driving the at least one rotating stone with the high torque motor, the driving causing the slurry (1) to be received via the respective axially aligned holes from the fluid conveyance, (2) to be directed onto flat grinding surfaces of the individual flat grindings stones, (3) to be ground while the suspended plant stock is in solution in the slurry, and (4) to be discharged from outer perimeters defined by the individual flat grindings stones of the set of flat grinding stones.

7. The method of claim 1, wherein the emitting microwave radiation, with at least one microwave emitter, toward at least a portion of the slurry while the suspended plant stock is ground by the wet-grinding apparatus comprises:
   emitting, with the at least one microwave emitter, at least some microwave radiation in a range between 300 GHz and 300 MHz.

8. The method of claim 1, wherein the emitting microwave radiation, with at least one microwave emitter, toward at least a portion of the slurry while the suspended plant stock is ground by the wet-grinding apparatus comprises:
   emitting, with the at least one microwave emitter, at least some microwave radiation with a photon energy of between 1.24 to −1.24 micro electron volts.

9. A method for extracting useful products from at least one of invasive, poisonous or toxic plant stock, the method comprising:
   conveying a slurry that contains at least one or more carrier liquids and at least some plant stock suspended in the one or more carrier liquids, the conveying being performed at least in part with a fluid conveyance of a wet-grinding apparatus;
   driving at least one rotor disk of a set of flat grinding disks of the wet-grinding apparatus with a motor drive operably coupled with a high torque motor, the driving causing the set of flat grinding disks to accept the slurry on one or more surfaces, to grind the suspended plant stock, and to discharge the slurry; and emitting microwave radiation, with at least one microwave emitter, toward at least a portion of the slurry at least one of before, while, or after the suspended plant stock is ground by the wet-grinding apparatus,
wherein the emitting microwave radiation, with at least one microwave emitter, toward at least a portion of the slurry at least one of before, while, or after the suspended plant stock is ground by the wet-grinding apparatus comprises:
emitting the microwave radiation within a containment structure configured to contain the microwave radiation and gases off-gassed from the slurry during microwave radiation treatment;
creating a negative atmosphere between 760 and 10-9 torr within the containment structure with a compressor; and
converting the off-gassed gases to liquid form for capture with at least a vapor recovery unit that includes at least one condenser.

10. The method of claim 1, wherein the emitting microwave radiation, with at least one microwave emitter, toward at least a portion of the slurry while the suspended plant stock is ground by the wet-grinding apparatus comprises:

conveying the slurry through one or more high temperature-resistant conveyances that include at least one of tubes, coils, or troughs that are transparent to microwave radiation; and emitting, with the at least one microwave emitter, microwave radiation toward at least a portion of the one or more conveyances, wherein the emitting of microwave radiation causes cells of the ground plant stocks in the slurry within the one or more conveyances to expand thereby making a wet-grinding more effective.

11. The method of claim 10, further comprising:

emitting the microwave radiation toward at least the portion of the one or more conveyances before processing of the slurry in the wet-grinding apparatus; and after the emitting of the microwave radiation, conveying the slurry, to an intake of the wet-grinding apparatus.

12. The method of claim 10, further comprising:

receiving the slurry in the one or more conveyances for exposure to microwave radiation after grinding in the wet-grinding apparatus; and emitting the microwave radiation toward at least the portion of the one or more conveyances.

13. The method of claim 1, wherein the emitting microwave radiation, with at least one microwave emitter, toward at least a portion of the slurry while the suspended plant stock is ground by the wet-grinding apparatus comprises:

emitting microwave radiation, with at least one microwave emitter of a microwave unit that is operating in at least one of a batch, batch-continuous or a continuous operation mode.

14. The method of claim 1, wherein the emitting microwave radiation, with at least one microwave emitter, toward the slurry, while the slurry is being ground by the wet-grinding apparatus comprises:

emitting the microwave radiation toward the slurry while the slurry is at least partially within the wet-grinding apparatus, the wet-grinding apparatus being encased in an encasement configured for containing the microwave radiation; and wherein the emitting of the microwave radiation toward the slurry causes cell fibers within the slurry to expand and thereby increase an effectiveness of grinding.

15. The method of claim 1, wherein the method further comprises:

primarily reducing a volume of plant stock by at least one of shredding or chopping the plant stock into pieces of less than 6 inches in length.

16. The method of claim 15, wherein the method further comprises:

secondarily reducing a volume of plant stock that has previously undergone primary reduction by at least one of shredding or compacting the plant stock with at least one of a rotary shear, a compactor, or a hammer mill.

17. The method of claim 16, wherein the method further comprises:

tertiarily reducing plant stock with at least one of a granulator, a grinder, or a knife mill to further reduce secondarily reduced plant stock to reduce the plant stock to a particle size adapted for wet-grinding with wet-grinding apparatus.

18. The method of claim 17, wherein the tertiarily reducing plant stock with at least one of a granulator, a grinder, or a knife mill to further reduce secondarily reduced plant stock to reduce the plant stock to a particle size adapted for wet-grinding with wet-grinding apparatus comprises:

capturing air-suspended particles escaping from tertiary reduction of plant stock with at least one of a cyclone or a baghouse.

19. The method of claim 1, wherein the method further comprises:

receiving the one or more carrier liquids and reduced plant stock in one or more containers;

mixing said one or more carrier liquids and reduced plant stock in said one or more containers to form a slurry of which the suspended plant stock is between 1% and 25% by weight.

20. The method of claim 19, wherein the mixing said one or more carrier liquids and reduced plant stock in said one or more containers to form a slurry of which the suspended plant stock is between 1% and 25% by weight comprises:

mixing said one or more carrier liquids and reduced plant stock with at least one of a hydro-pulper or a high-agitation mixer.

21. The method of claim 19, wherein the mixing said one or more carrier liquids and reduced plant stock in said one or more containers to form a slurry of which the suspended plant stock is between 1% and 25% by weight comprises:

at least partially separating, with a centrifugal separator, at least one of earthly inerts or non-plant materials from the slurry.

22. The method of claim 19, wherein the mixing said one or more carrier liquids and reduced plant stock in said one or more containers to form a slurry of which the suspended plant stock is between 1% and 25% by weight comprises:

mixing into at least one of the one or more carrier liquids or the slurry at least one of a surfactant, an additive, vegetation containing sugars, or an amylase type additive.

23. The method of claim 1, wherein the method further comprises:

separating the slurry into (1) a wet fiber suitable for further processing into one or more first products and (2) a liquid fraction suitable for further processing into one or more second products.

24. A method for extracting useful products from at least one of invasive, poisonous or toxic plant stock, the method comprising:

conveying a slurry that contains at least one or more carrier liquids and at least some plant stock suspended in the one or more carrier liquids, the conveying being performed at least in part with a fluid conveyance of a wet-grinding apparatus;

driving at least one rotor disk of a set of flat grinding disks of the wet-grinding apparatus with a motor drive operably coupled with a high torque motor, the driving causing the set of flat grinding disks to accept the slurry on one or more surfaces, to grind the suspended plant stock, and to discharge the slurry;

emitting microwave radiation, with at least one microwave emitter, toward at least a portion of the slurry at least one of before, while, or after the suspended plant stock is ground by the wet-grinding apparatus; and separating the slurry into (1) a wet fiber suitable for further processing into one or more first products and (2) a liquid fraction suitable for further processing into one or more second products, wherein the separating the slurry into (1) a wet fiber suitable for further processing into one or more first products and (2) a liquid fraction suitable for further processing into one or more second products comprises:

separating the slurry at least in part with a separator apparatus that includes at least one of a decanting centrifuge, a basket centrifuge, or an SS Buchner Funnel method.

25. The method of claim 23, wherein the method further comprises:

extracting at least one of an oxalic acid fraction, an oxalic salt fraction, or organic compounds from the liquid fraction with at least one of ultrasonic settling, centrifuging, or liquid-liquid separation.

26. The method of claim 23, wherein the separating the slurry into (1) a wet fiber suitable for further processing into one or more first products and (2) a liquid fraction suitable for further processing into one or more second products comprises:

directing ultrasonic waves having a frequency between 20 Hz and 200 Mhz toward the slurry, wherein the ultrasonic waves aid separation of the slurry into the liquid fraction and the wet fiber.

27. The method of claim 23, wherein the method further comprises:

directing germicidal ultraviolet light radiation toward at least one of the slurry, the liquid fraction or the wet fiber, wherein the ultraviolet light is configured to reduce a risk of at least one of bacterial or fungal growth.

28. The method of claim 27, wherein the directing germicidal ultraviolet light radiation toward at least one of the slurry, the liquid fraction or the wet fiber, wherein the ultraviolet light is configured to reduce a risk of at least one of bacterial or fungal growth comprises:

directing at least some ultraviolet waves of the ultraviolet light waves that have one or more wave lengths in a range between 100 and 2809 nanometers.

29. The method of claim 23, wherein the method further comprises:

creating a negative atmosphere in one or more chambers containing at least some of the slurry to facilitate capture of at least some light volatiles escaping from at least one of the slurry or the extracted liquid fraction; and converting at least some of the captured light volatiles into one or more liquid forms.

30. The method of claim 23, wherein the separating the slurry into (1) a wet fiber suitable for further processing into one or more first products and (2) a liquid fraction suitable for further processing into one or more second products comprises:

separating the slurry into a wet fiber suitable for further processing into one or more first products that include at least one of gluten-free flour, pellets for agricultural feed, fillers for foodstuffs, plastics, adhesives, ethanol, or distilled spirits.

31. The method of claim 23, wherein the separating the slurry into (1) a wet fiber suitable for further processing into one or more first products and (2) a liquid fraction suitable for further processing into one or more second products comprises:

separating the slurry into a liquid fraction suitable for further processing into one or more second products that include at least one of a pesticide, an insecticide or a fungicide.

32. The method of claim 23, wherein the separating the slurry into (1) a wet fiber suitable for further processing into one or more first products and (2) a liquid fraction suitable for further processing into one or more second products comprises:

separating the slurry into a wet fiber suitable for further processing into at least one of liquid, solid, crystal, powdery, granular, or oily products.

33. The method of claim 23, wherein the separating the slurry into (1) a wet fiber suitable for further processing into one or more first products and (2) a liquid fraction suitable for further processing into one or more second products comprises:

separating the slurry into a wet fiber suitable for further processing into one or more materials that can be blended with at least one of an organic material, a dry material, a wet material, or a liquid to produce one or more complex compounds.

34. The method of claim 1, wherein the at least one of an invasive, a poisonous or a toxic plant stock includes at least one of tumbleweed (salsula targus), kudzu, rosemary bean (*Abrus precatorius*) or sage brush plant stock.

* * * * *